United States Patent [19]
Dalie et al.

[11] Patent Number: 5,863,537
[45] Date of Patent: Jan. 26, 1999

[54] HUMANIZED MONOCLONAL ANTIBODIES AGAINST HUMAN INTERLEUKIN-4

[75] Inventors: Barbara Dalie, Maywood; Hung V. Le, Rockway; Kenneth Miller, Edison; Nicholas J. Murgolo, Millington, all of N.J.; Hanh Nguyen, Brookline, Mass.; Stephen Tindall, Madison; Paul J. Zavodny, Mountainside, both of N.J.

[73] Assignee: Schering Corporation, Kenilworth, N.J.

[21] Appl. No.: 290,793

[22] PCT Filed: Feb. 18, 1993

[86] PCT No.: PCT/US93/01301

§ 371 Date: Aug. 16, 1994

§ 102(e) Date: Aug. 16, 1994

[87] PCT Pub. No.: WO93/17106

PCT Pub. Date: Sep. 2, 1993

Related U.S. Application Data

[63] Continuation-in-part of Ser. No. 841,659, Feb. 19, 1992, abandoned.

[51] Int. Cl.$^6$ ............... A61K 39/395; A61K 39/40; C07K 16/00; C12P 21/08
[52] U.S. Cl. ............ 424/133.1; 424/135.1; 424/141.1; 424/145.1; 424/152.1; 424/172.1; 530/350; 530/387.1; 530/387.3; 530/388.23
[58] Field of Search ............... 424/133.1, 141.1, 424/135.1, 145.1, 152.1, 172.1; 530/387.3, 388.1, 388.23, 350, 387.1

[56] References Cited

U.S. PATENT DOCUMENTS 5,041,381  8/1991  Abrams et al. .
5,585,089  12/1996  Queen et al. .

FOREIGN PATENT DOCUMENTS 0 314 402   5/1989  European Pat. Off. .
0 332 424   9/1989  European Pat. Off. .
WO 89/03846  5/1989  WIPO .
WO 93/17106  9/1993  WIPO .

OTHER PUBLICATIONS

Casali et al., Science 234:476 (1986).
Jameson et al., Nature 341:465 (1989).
Kabat et al.. *Sequences of Proteins of Immunological Interest,* 4h Edition, U.S. Dept. of Health and Human Services, National Institutes of Health (1987), pp. vii–xliv.
Lewis et al., Gene 101:297 (1991).
Queen et al., Proc. Natl. Acad. Sci. USA 86:10029 (1989).
Riechmann et al., Nature 332:323 (1988).
Saiki et al., Science 239:487 (1988).
Bird et al., 1988, *Science* 242:423–426.
Bird and Walker, 1991, *Tibtech* 9:132–137.
Lazar et al (Molecular & Cellular Biology vol. 8 Mar. 1988 pp. 1247–1252).
Burgess et al (J. of Cell Biology vol. 111 Nov. 1990 pp. 2129–2138).

*Primary Examiner*—Anthony C. Caputa
*Assistant Examiner*—Mark Navarro
*Attorney, Agent, or Firm*—Norman C. Dulak; Donald W. Wyatt; Cynthia L. Foulke

[57] ABSTRACT

Monoclonal antibodies are provided which are specific for human interleukin-4. Also provided are complementary DNAs which encode the heavy and light chain variable regions of such monoclonal antibodies and complementarity determining regions from such DNAs; and kits and methods for detecting, measuring and immunopurifying human interleukin-4, and for blocking the biological activity of human interleukin-4.

5 Claims, 6 Drawing Sheets

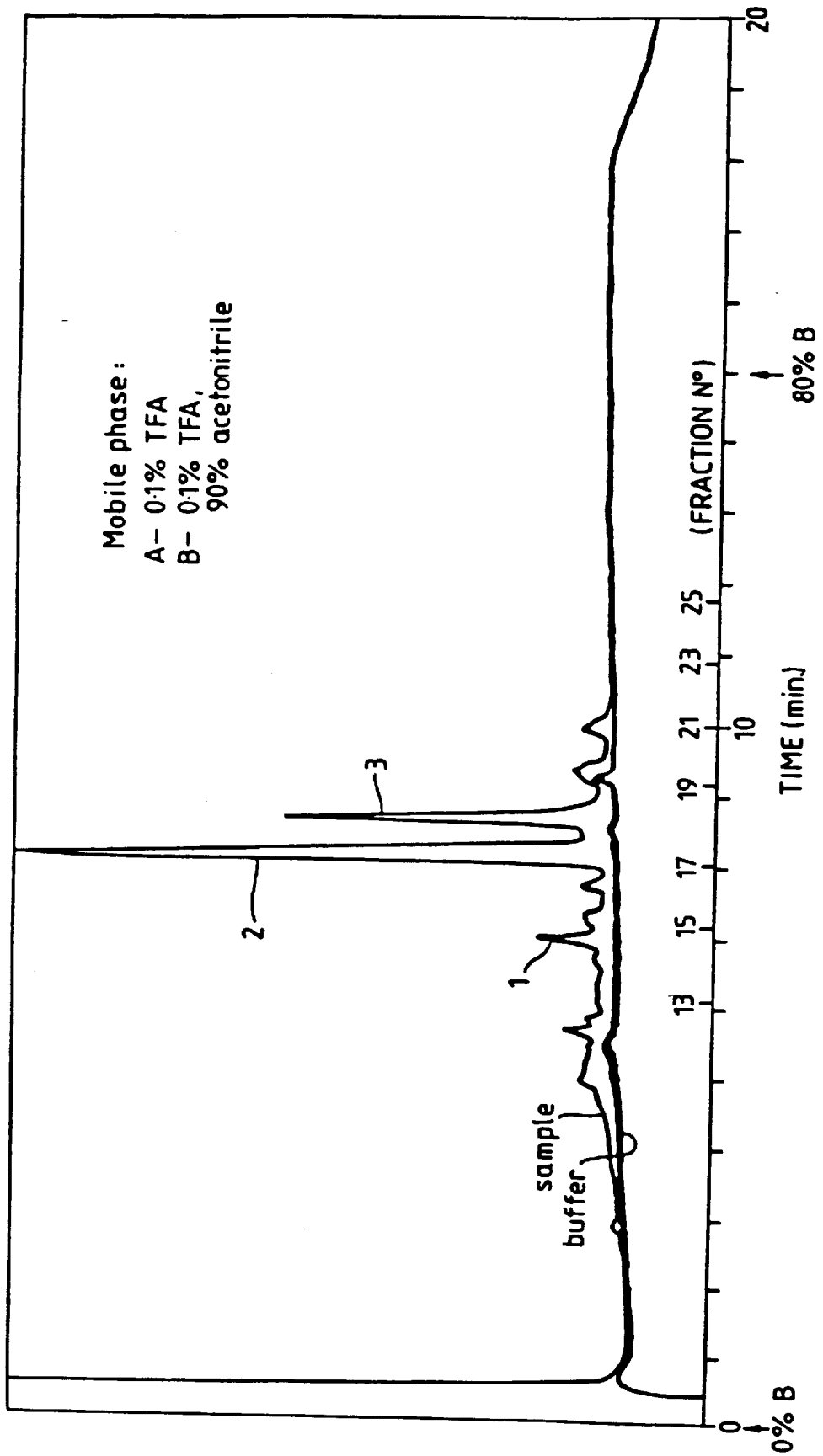

Fig. 6

|  | CDR1 | CDR2 | CDR3 |
|---|---|---|---|
| LAY | GFTFSASAMS | WKYENGNDKHYADSVN | DAGPYVSPTFFAH |
| 25D2 | S RSYW T | SISIS DNTY P R | P–Y F GHY DF |
| h.25D2H-1 | S RSYW T | SISIS DNTY P R | P–Y F GHY DF |
| h25D2H-2 | S RSY | SISIS DNTY P R | P–Y F GHY DF |
| h25D2H-3 | SYW T | SISIS DNTY P R | P–Y F GHY DF |
| h25D2H-4 | SYW T | SISIS DNTY P | P–Y F GHY DF |
| h25D2H-5 | S RSY | SISIS DNTY P | P–Y F GHY DF |

― CDR Loop
═ Overlap of CDR Loop and Kabat Region
• Kabat Region

SEQUENCE LISTING ( 1 ) GENERAL INFORMATION:

( i i i ) NUMBER OF SEQUENCES: 69

( 2 ) INFORMATION FOR SEQ ID NO: 1:

( i ) SEQUENCE CHARACTERISTICS:
        ( A ) LENGTH: 363 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GAA  CTG  CAG  TTG  GTA  GAA  AGT  GGG  GGA  GGT  CTG  GTG  CAG  CCT  GGA  AGG        48
Glu  Leu  Gln  Leu  Val  Glu  Ser  Gly  Gly  Gly  Leu  Val  Gln  Pro  Gly  Arg
                    5                        10                       15

TCT  CTG  AAA  CTA  TCC  TGT  GTG  GCC  TCT  GGA  TTC  TCA  TTC  AGA  AGT  TAC        96
Ser  Leu  Lys  Leu  Ser  Cys  Val  Ala  Ser  Gly  Phe  Ser  Phe  Arg  Ser  Tyr
               20                        25                       30

TGG  ATG  ACC  TGG  GTC  CGT  CAG  GCT  CCA  GGG  AAG  GGG  CTG  GAG  TGG  ATT       144
Trp  Met  Thr  Trp  Val  Arg  Gln  Ala  Pro  Gly  Lys  Gly  Leu  Glu  Trp  Ile
          35                       40                            45

GCA  TCC  ATT  AGT  ATT  TCT  GGT  GAT  AAC  ACG  TAC  TAT  CCA  GAC  TCT  GTG       192
Ala  Ser  Ile  Ser  Ile  Ser  Gly  Asp  Asn  Thr  Tyr  Tyr  Pro  Asp  Ser  Val
     50                        55                             60

AGG  GGC  CGA  TTC  ACT  ATC  TCC  AGG  GAT  GAT  GCA  AAA  AGC  ATC  CTA  TAC       240
Arg  Gly  Arg  Phe  Thr  Ile  Ser  Arg  Asp  Asp  Ala  Lys  Ser  Ile  Leu  Tyr
65                        70                        75                       80

CTT  CAA  ATG  AAC  AGT  CTG  AGG  TCT  GAG  GAC  ACG  GCC  ACT  TAT  TAC  TGT       288
Leu  Gln  Met  Asn  Ser  Leu  Arg  Ser  Glu  Asp  Thr  Ala  Thr  Tyr  Tyr  Cys
                    85                        90                       95

GTA  AGA  GAT  CCC  TAT  TAC  TTC  AGT  GGC  CAC  TAC  TTT  GAT  TTC  TGG  GGC       336
Val  Arg  Asp  Pro  Tyr  Tyr  Phe  Ser  Gly  His  Tyr  Phe  Asp  Phe  Trp  Gly
               100                       105                      110

CAA  GGA  GTC  ATG  GTC  ACA  GTC  TCC  TCA                                          363
Gln  Gly  Val  Met  Val  Thr  Val  Ser  Ser
```

( 2 ) INFORMATION FOR SEQ ID NO: 2:

( i ) SEQUENCE CHARACTERISTICS:
        ( A ) LENGTH: 321 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
GAT  ATC  CAG  ATG  ACA  CAG  AGT  CCT  TCA  CTC  CTG  TCT  GCA  TCT  GTG  GGA      48
Asp  Ile  Gln  Met  Thr  Gln  Ser  Pro  Ser  Leu  Leu  Ser  Ala  Ser  Val  Gly
               5                        10                      15

GAC  AGA  GTC  ACT  CTC  AAC  TGC  AAA  GCA  AGT  CAG  AAT  ATT  TAT  AAG  AAT      96
Asp  Arg  Val  Thr  Leu  Asn  Cys  Lys  Ala  Ser  Gln  Asn  Ile  Tyr  Lys  Asn
               20                       25                      30

TTA  GCC  TGG  TAT  CAG  CAA  AAG  CTT  GGA  GAA  GCT  CCC  AAG  TTC  CTG  ATT     144
Leu  Ala  Trp  Tyr  Gln  Gln  Lys  Leu  Gly  Glu  Ala  Pro  Lys  Phe  Leu  Ile
               35                       40                      45

TTT  AAT  GCA  AAA  AGT  TTG  GAG  ACG  GGC  GTC  CCA  TCA  AGG  TTC  AGT  GGC     192
Phe  Asn  Ala  Lys  Ser  Leu  Glu  Thr  Gly  Val  Pro  Ser  Arg  Phe  Ser  Gly
         50                       55                       60

AGT  GGA  TCT  GGC  ACA  GAT  TTC  ACA  CTC  ACA  ATC  AGC  AGC  CTA  CAG  CCT     240
Ser  Gly  Ser  Gly  Thr  Asp  Phe  Thr  Leu  Thr  Ile  Ser  Ser  Leu  Gln  Pro
65                            70                       75                      80

GAA  GAT  GTT  GCC  ACA  TAT  TTC  TGC  CAA  CAA  TAT  TAT  AGC  GGG  TGG  ACG     288
Glu  Asp  Val  Ala  Thr  Tyr  Phe  Cys  Gln  Gln  Tyr  Tyr  Ser  Gly  Trp  Thr
                         85                       90                      95

TTC  GGT  GGA  GGC  ACC  AAG  CTG  GAA  TTG  AAA  CGG                              321
Phe  Gly  Gly  Gly  Thr  Lys  Leu  Glu  Leu  Lys  Arg
               100                      105
```

( 2 ) INFORMATION FOR SEQ ID NO: 3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
CGATGCACAA  GTGCGAT                                                                 17
```

( 2 ) INFORMATION FOR SEQ ID NO: 4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
ATCGCACTTG  TGCAT                                                                   15
```

( 2 ) INFORMATION FOR SEQ ID NO: 5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
GCACTAGTTC  TAGAAGGCCA  AGAGGGGCCA  CTGACTCTGG  GGTCAT                              46
```

( 2 ) INFORMATION FOR SEQ ID NO: 6:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GCGCGGCCGC GARYTNCARY TNGTNGARWS NGGNGGNGGN CTNGTNCARC C        51

( 2 ) INFORMATION FOR SEQ ID NO: 7:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GCACTAGTTC TAGATTGGGT CTAACACTCA TTCCTGTTGA AGCTCTTGAC G        51

( 2 ) INFORMATION FOR SEQ ID NO: 8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

GCGCGGCCGC GAYATHCARA TGACNCARAG YCC        33

( 2 ) INFORMATION FOR SEQ ID NO: 9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GGAAGGTCTC TGAAACTATC        20

( 2 ) INFORMATION FOR SEQ ID NO: 10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

AGACAGAGTC ACTCTC        16

( 2 ) INFORMATION FOR SEQ ID NO: 11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CCTTCAAATG AAC        13

( 2 ) INFORMATION FOR SEQ ID NO: 12:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 12:

GTTCATTTGA AGG     13

( 2 ) INFORMATION FOR SEQ ID NO: 13:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 13:

GCCTGAAGAT GTTGCCAC     18

( 2 ) INFORMATION FOR SEQ ID NO: 14:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 14:

ATTAACCCTC ACTAAAG     17

( 2 ) INFORMATION FOR SEQ ID NO: 15:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 15:

AATACGACTC ACTATAG     17

( 2 ) INFORMATION FOR SEQ ID NO: 16:

( i ) SEQUENCE CHARACTERISTICS:
    ( A ) LENGTH: 390 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 16:

```
GAATTCGCCG CCACC ATG GGA TGG AGC TGT ATC ATC CTC TTC TTG GTA        48
                Met Gly Trp Ser Cys Ile Ile Leu Phe Leu Val
                                -15                 -10

GCA ACA GCT ACA GGT GTC CAC TCC GAT ATC CAG ATG ACC CAG AGC CCA     96
Ala Thr Ala Thr Gly Val His Ser Asp Ile Gln Met Thr Gln Ser Pro
            -5                   1               5

AGC AGC CTG AGC GTG AGC GTG GGT GAC CGC GTG ACC ATC ACC TGC AAG     144
Ser Ser Leu Ser Val Ser Val Gly Asp Arg Val Thr Ile Thr Cys Lys
        10              15                  20

GCC AGC CAG AAC ATC TAC AAG AAC CTG GCC TGG TAC CAG CAG AAG CCA     192
Ala Ser Gln Asn Ile Tyr Lys Asn Leu Ala Trp Tyr Gln Gln Lys Pro
25                  30                  35                  40

GGC CTG GCC CCA AAG TTC CTG ATC TTC AAC GCC AAG AGC CTG GAG ACC     240
Gly Leu Ala Pro Lys Phe Leu Ile Phe Asn Ala Lys Ser Leu Glu Thr
            45                  50                  55
```

```
GGC GTG CCA TCT AGA TTC AGC GGC AGC GGC AGC GGC ACC GAC TTC ACC      288
Gly Val Pro Ser Arg Phe Ser Gly Ser Gly Ser Gly Thr Asp Phe Thr
            60                  65                  70

TTC ACC ATC AGC AGC CTG CAG CCA GAG GAC ATC GCC ACC TAC TAC TGC      336
Phe Thr Ile Ser Ser Leu Gln Pro Glu Asp Ile Ala Thr Tyr Tyr Cys
        75                  80                  85

CAG CAG TAC TAC AGC GGC TGG ACC TTT GGC CAA GGC ACC AAG GTG GAG      384
Gln Gln Tyr Tyr Ser Gly Trp Thr Phe Gly Gln Gly Thr Lys Val Glu
        90                  95                 100

GTG AAG                                                               390
Val Lys
105
```

(2) INFORMATION FOR SEQ ID NO: 17:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 17:

```
GAACAAAAGC TTGACATCCA GATGACCCAG AGCCCAAGCA GCCTGAGCGT GAGCGTGGGT      60
GACCGCGTGA CC                                                          72
```

(2) INFORMATION FOR SEQ ID NO: 18:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (xi) SEQUENCE DESCRIPTION: SEQ ID NO: 18:

```
GAGCTCGGTA CCAGGCCAGG TTCTTGTAGA TGTTCTGGCT GGCCTTGCAG GTGATGGTCA      60
CGCGGTCACC CAC                                                         73
```

(2) INFORMATION FOR SEQ ID NO: 19:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO: 19:

```
GGTACCGGTC CGGAATTCGC CGCCACCATG GGATGGAGCT GTATCATCCT CTTCTTGGTA      60
GCAACAGCTA CAGGTGTCCA CTCCGATATC CAGATGACCC AGAGC                     105
```

(2) INFORMATION FOR SEQ ID NO: 20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 20:

```
CTGCTGGTAC CAGGCCAGGT TCTTGTAGAT GTTCTG                                36
```

(2) INFORMATION FOR SEQ ID NO: 21:

(i) SEQUENCE CHARACTERISTICS:
        (A) LENGTH: 80 base pairs (  B  ) TYPE: nucleic acid
(  C  ) STRANDEDNESS: single
(  D  ) TOPOLOGY: linear (  x i  ) SEQUENCE DESCRIPTION: SEQ ID NO: 21:

TCCCCGGGTA CCAGCAGAAG CCAGGCCTGG CCCCAAAGTT CCTGATCTTC AACGCCAAGA        60

GCCTGGAGAC CGGCGTGCCA        80

(  2  ) INFORMATION FOR SEQ ID NO: 22:

(  i  ) SEQUENCE CHARACTERISTICS:
(  A  ) LENGTH: 84 base pairs
(  B  ) TYPE: nucleic acid
(  C  ) STRANDEDNESS: single
(  D  ) TOPOLOGY: linear (  x i  ) SEQUENCE DESCRIPTION: SEQ ID NO: 22:

GTCGACCTGC AGGCTGCTGA TGGTGAAGGT GAAGTCGGTG CCGCTGCCGC TGCCGCTGAA        60

TCTAGATGGC ACGCCGGTCT CCAG        84

(  2  ) INFORMATION FOR SEQ ID NO: 23:

(  i  ) SEQUENCE CHARACTERISTICS:
(  A  ) LENGTH: 68 base pairs
(  B  ) TYPE: nucleic acid
(  C  ) STRANDEDNESS: single
(  D  ) TOPOLOGY: linear (  x i  ) SEQUENCE DESCRIPTION: SEQ ID NO: 23:

ACCATCAGCA GCCTGCAGCC AGAGGACATC GCCACCTACT ACTGCCAGCA GTACTACAGC        60

GGCTGGAC        68

(  2  ) INFORMATION FOR SEQ ID NO: 24:

(  i  ) SEQUENCE CHARACTERISTICS:
(  A  ) LENGTH: 74 base pairs
(  B  ) TYPE: nucleic acid
(  C  ) STRANDEDNESS: single
(  D  ) TOPOLOGY: linear (  x i  ) SEQUENCE DESCRIPTION: SEQ ID NO: 24:

CAGAGTTTAG AATTCACTCA CGCTTCACCT CCACCTTGGT GCCTTGGCCA AAGGTCCAGC        60

CGCTGTAGTA CTGC        74

(  2  ) INFORMATION FOR SEQ ID NO: 25:

(  i  ) SEQUENCE CHARACTERISTICS:
(  A  ) LENGTH: 33 base pairs
(  B  ) TYPE: nucleic acid
(  C  ) STRANDEDNESS: single
(  D  ) TOPOLOGY: linear (  x i  ) SEQUENCE DESCRIPTION: SEQ ID NO: 25:

GTCGAATTCT CAACACTCTC CCCTGTTGAA GCT        33

(  2  ) INFORMATION FOR SEQ ID NO: 26:

(  i  ) SEQUENCE CHARACTERISTICS:
(  A  ) LENGTH: 59 base pairs
(  B  ) TYPE: nucleic acid
(  C  ) STRANDEDNESS: single
(  D  ) TOPOLOGY: linear (  x i  ) SEQUENCE DESCRIPTION: SEQ ID NO: 26:

GTTTTGGCCA AGGCACCAAG GTGGAGGTGA AGACTGTGGC TGCACCATCT GTCTTCATC        59

( 2 ) INFORMATION FOR SEQ ID NO: 27:

( i ) SEQUENCE CHARACTERISTICS:
    ( A ) LENGTH: 393 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 27:

```
GAATTCGCCG CCACC ATG GGA TGG AGC TGT ATC ATC CTC TTC TTG GTA                    48
                Met Gly Trp Ser Cys Ile Ile Leu Phe Leu Val
                 -15                              -10

GCA ACA GCT ACA GGT GTC CAC TCC GAT ATC CAG ATG ACC CAG AGC CCA                 96
Ala Thr Ala Thr Gly Val His Ser Asp Ile Gln Met Thr Gln Ser Pro
         -5                   1                   5

AGC AGC CTG AGC GTG AGC GTG GGT GAC CGC GTG ACC ATC ACC TGC AAG                144
Ser Ser Leu Ser Val Ser Val Gly Asp Arg Val Thr Ile Thr Cys Lys
        10                  15                  20

GCC AGC CAG AAC ATC TAC AAG AAC CTG GCC TGG TAC CAG CAG AAG CCA                192
Ala Ser Gln Asn Ile Tyr Lys Asn Leu Ala Trp Tyr Gln Gln Lys Pro
 25                  30                  35                  40

GGC CTG GCC CCA AAG CTG CTG ATC TAC AAC GCC AAG AGC CTG GAG ACC                240
Gly Leu Ala Pro Lys Leu Leu Ile Tyr Asn Ala Lys Ser Leu Glu Thr
                 45                  50                  55

GGC GTG CCA TCT AGA TTC AGC GGC AGC GGC AGC GGC ACC GAC TTC ACC                288
Gly Val Pro Ser Arg Phe Ser Gly Ser Gly Ser Gly Thr Asp Phe Thr
                60                  65                  70

TTC ACC ATC AGC AGC CTG CAG CCA GAG GAC ATC GCC ACC TAC TAC TGC                336
Phe Thr Ile Ser Ser Leu Gln Pro Glu Asp Ile Ala Thr Tyr Tyr Cys
             75                  80                  85

CAG CAG TAC TAC AGC GGC TGG ACC TTT GGC CAA GGC ACC AAG GTG GAG                384
Gln Gln Tyr Tyr Ser Gly Trp Thr Phe Gly Gln Gly Thr Lys Val Glu
         90                  95                 100

GTG AAG CGC                                                                    393
Val Lys Arg
105
```

( 2 ) INFORMATION FOR SEQ ID NO: 28:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 28:

```
AAGCCAGGCC TGGCCCCAAA GCTGCTGATC TACAACGCC                                      39
```

( 2 ) INFORMATION FOR SEQ ID NO: 29:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 29:

```
TGGCTGCAGG CTGCT                                                                15
```

( 2 ) INFORMATION FOR SEQ ID NO: 30:

( i ) SEQUENCE CHARACTERISTICS:
    ( A ) LENGTH: 45 base pairs
    ( B ) TYPE: nucleic acid ( C ) STRANDEDNESS: single
( D ) TOPOLOGY: linear ( x i ) SEQUENCE DESCRIPTION: SEQ ID NO: 30:

```
ACCTTTGGCC AAGGCACCAA GGTGGAGGTG AAGCGCACTG TGGCT                    45
```

( 2 ) INFORMATION FOR SEQ ID NO: 31:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 31:

```
TCTAGAACTA GTGGATCC                                                  18
```

( 2 ) INFORMATION FOR SEQ ID NO: 32:

( i ) SEQUENCE CHARACTERISTICS:
        ( A ) LENGTH: 435 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 32:

```
GTCGACGCCG CCACC ATG GGA TGG AGC TGT ATC ATC CTC TTC TTG GTA         48
                Met Gly Trp Ser Cys Ile Ile Leu Phe Leu Val
                 -15                  -10

GCA ACA GCT ACA GGT GTC CAC TCC GAG GTG CAG CTG CTG GAG AGC GGC      96
Ala Thr Ala Thr Gly Val His Ser Glu Val Gln Leu Leu Glu Ser Gly
             -5              1               5

GGC GGC CTG GTG CAG CCA GGC GGA TCC CTG CGC CTG AGC TGC GCC GCC     144
Gly Gly Leu Val Gln Pro Gly Gly Ser Leu Arg Leu Ser Cys Ala Ala
 10                  15                  20

AGC GGC TTC AGC TTC CGC AGC TAC TGG ATG ACC TGG GTG CGC CAG GCC     192
Ser Gly Phe Ser Phe Arg Ser Tyr Trp Met Thr Trp Val Arg Gln Ala
 25              30                  35                  40

CCG GGC AAG GGC CTG GAG TGG GTG GCC AGC ATC AGC ATC AGC GGC GAC     240
Pro Gly Lys Gly Leu Glu Trp Val Ala Ser Ile Ser Ile Ser Gly Asp
                 45                  50                  55

AAC ACC TAC TAC CCA GAC AGC GTG CGC GGC CGC TTC ACC ATC AGC CGC     288
Asn Thr Tyr Tyr Pro Asp Ser Val Arg Gly Arg Phe Thr Ile Ser Arg
             60                  65                  70

AAC GAC AGC AAG AAC ACC CTG TAC CTG CAG ATG AAC GGC CTG CAA GCC     336
Asn Asp Ser Lys Asn Thr Leu Tyr Leu Gln Met Asn Gly Leu Gln Ala
         75                  80                  85

GAG GTG AGC GCC ATC TAC TAC TGC GCC CGC GAC CCA TAC TAC TTC AGC     384
Glu Val Ser Ala Ile Tyr Tyr Cys Ala Arg Asp Pro Tyr Tyr Phe Ser
 90                  95                 100

GGC CAC TAC TTC GAC TTC TGG GGC CAG GGT ACC CTG GTG ACC GTG AGC     432
Gly His Tyr Phe Asp Phe Trp Gly Gln Gly Thr Leu Val Thr Val Ser
105             110                 115                     120

AGC                                                                 435
Ser
```

( 2 ) INFORMATION FOR SEQ ID NO: 33:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 33:

ACTAGTGAAT TCGTCGACGC CGCCACCATG GGATGGAGCT GTATCATCCT CTTCTTGGTA    60

GCAACAGCTA CAGGTGTCCA CTCC    84

( 2 ) INFORMATION FOR SEQ ID NO: 34:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 34:

GCAGCTCAGG CGCAGGGATC CGCCTGGCTG CACCAGGCCG CCGCCGCTCT CCAGCAGCTG    60

CACCTCGGAG TGGACACCTG TAGC    84

( 2 ) INFORMATION FOR SEQ ID NO: 35:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 35:

AGCGTCGACG CCGCCACCAT G    21

( 2 ) INFORMATION FOR SEQ ID NO: 36:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 36:

GTATCCCCCG GGGCCTGGCG CACCCAGGTC ATCCAGTAGC TGCGGAAGCT GAAGCCGCTG    60

GCGGCGCAGC TCAGGCGCAG    80

( 2 ) INFORMATION FOR SEQ ID NO: 37:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 37:

GTATCCCCCG GGCAAGGGCC TGGAGTGGGT GGCCAGCATC AGCATCAGCG GCGACAACAC    60

CTACTACCCA GACAGCGTG    79

( 2 ) INFORMATION FOR SEQ ID NO: 38:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 38:

GTAGAACTGC AGGTACAGGG TGTTCTTGCT GTCGTTGCGG CTGATGGTGA AGCGGCCGCG    60

CACGCTGTCT GGGTAGTA    78

( 2 ) INFORMATION FOR SEQ ID NO: 39:

( i ) SEQUENCE CHARACTERISTICS:
   ( A ) LENGTH: 84 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 39:

AACACCCTGT ACCTGCAGAT GAACGGCCTG CAAGCCGAGG TGAGCGCCAT CTACTACTGC           60

GCCCGCGACC CATACTACTT CAGC           84

( 2 ) INFORMATION FOR SEQ ID NO: 40:

( i ) SEQUENCE CHARACTERISTICS:
      ( A ) LENGTH: 60 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 40:

GTCACCAGGG TACCCTGGCC CCAGAAGTCG AAGTAGTGGC CGCTGAAGTA GTATGGGTCG           60

( 2 ) INFORMATION FOR SEQ ID NO: 41:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 41:

CTGTACCTGC AGATGAACGG CCTGCAAGCC GAGGTG           36

( 2 ) INFORMATION FOR SEQ ID NO: 42:

( i ) SEQUENCE CHARACTERISTICS:
      ( A ) LENGTH: 60 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 42:

GGGGAAGACG GATGGGCCCT TGGTGGAAGC GCTGCTCACG GTCACCAGGG TACCCTGGCC           60

( 2 ) INFORMATION FOR SEQ ID NO: 43:

( i ) SEQUENCE CHARACTERISTICS:
      ( A ) LENGTH: 102 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 43:

GCTGAATTCG CCGCCACCAT GGGCTGGAGC TGTATCATCC TCTTCTTAGT AGCAACAGCT           60

ACAGGTGTCC ACTCCCAGGT CAAACTGGTA CAAGCTGGAG GT           102

( 2 ) INFORMATION FOR SEQ ID NO: 44:

( i ) SEQUENCE CHARACTERISTICS:
      ( A ) LENGTH: 102 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 44:

GCGTACTAGT TAATGATAAC CCAGAGACGA TGCAACTCAG TCGCAGAGAT CTTCCTGGCT           60

GTACGACGCC ACCTCCAGCT TGTACCAGTT TGACCTGGGA GT           102

( 2 ) INFORMATION FOR SEQ ID NO: 45:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 45:

GTCAGACTAG TAATAGTGTG AACTGGATAC GGCAAGCACC TGGCAAGGGT CTGGAGTGGG           60

TTGCACTAAT ATGGAGTAAT GGAGAC           86

( 2 ) INFORMATION FOR SEQ ID NO: 46:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 46:

GTACTCTAGA GATTGTGAAT CGAGATTTGA TAGCTGAATT ATAATCTGTG TCTCCATTAC           60

TCCATATTAG TGC           73

( 2 ) INFORMATION FOR SEQ ID NO: 47:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 47:

GCAGAATTCT AGAGACAATT CGAAGAGCAC CCTATACATG CAGATGAACA GTCTGAGAAC           60

TGAAGATACT GCAGTCTACT TCTGTGCTCG TGAGTACTAT GGAT           104

( 2 ) INFORMATION FOR SEQ ID NO:48:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 48:

CTCGTGAGCT CGGGCCCTTG GTCGACGCTG AGGAGACTGT GACTAGGACA CCTTGACCCC           60

AATAGTCGAA ATATCCATAG TACTCACGAG CACAGAAGT           99

( 2 ) INFORMATION FOR SEQ ID NO: 49:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 49:

GCATCGCGTC GACCAAAGGT CCATCTGTGT TTCCGCTGGC GCCATGCTCC AGGAGCACCT           60

CCGAGAGCAC           70

( 2 ) INFORMATION FOR SEQ ID NO: 50:

( i ) SEQUENCE CHARACTERISTICS:
  ( A ) LENGTH: 79 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 50:

GACAGAATTC AGGTGCTGGA CACGACGGAC ATGGAGGACC ATACTTCGAC TCAACTCTCT        60

TGTCCACCTT GGTGTTGCT        79

( 2 ) INFORMATION FOR SEQ ID NO: 51:

( i ) SEQUENCE CHARACTERISTICS:
    ( A ) LENGTH: 68 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 51:

ACTGGAATTC CTAGGTGGAC CATCAGTCTT CCTGTTTCCG CCTAAGCCCA AGGACACTCT        60

CATGATCT        68

( 2 ) INFORMATION FOR SEQ ID NO: 52:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 52:

CAGGCTGTCG ACTCGAGGCT GACCTTTGGC TTTGGAGATG GTTTTCTCGA T        51

( 2 ) INFORMATION FOR SEQ ID NO: 53:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 53:

GTAAGCGTCG ACTCGAGAGC CACAGGTGTA CACCCTGC        38

( 2 ) INFORMATION FOR SEQ ID NO: 54:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 54:

CGCTAGCGGC CGCTCATTTA CCCAGAGACA GGGAGAGGCT        40

( 2 ) INFORMATION FOR SEQ ID NO: 55:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 55:

GATCCCTGCG CCTGAGCTGC GCCGCTAGCG GCTTCAGCTT CCGCAGCTAC GCCATGAGCT        60

GGGTGCGCCA GGCCCC        76

( 2 ) INFORMATION FOR SEQ ID NO: 56:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 56:

```
GGGGCCTGGC GCACCCAGCT CATGGCGTAG CTGCGGAAGC TGAAGCCGCT AGCGGCGCAG        60

CTCAGGCGCA GG                                                           72
```

( 2 ) INFORMATION FOR SEQ ID NO: 57:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 57:

```
CTAGCGGCTT CACCTTCAGC AGCTACTGGA TGACCTGGGT GCGCCAGGCC CC               52
```

( 2 ) INFORMATION FOR SEQ ID NO: 58:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 58:

```
GGGGCCTGGC GCACCCAGGT CATCCAGTAG CTGCTGAAGG TGAAGCCG                    48
```

( 2 ) INFORMATION FOR SEQ ID NO: 59:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 59:

```
CCAGCATCAG CATCAGCGGC GACAACACCT ACTACCCAGA CAGCGTGAAC GGCCGCTTCA        60

CCATCTCTAG AAACGACAGC AAGAACACCC TGTACCTGCA                            100
```

( 2 ) INFORMATION FOR SEQ ID NO: 60:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 60:

```
GGTACAGGGT GTTCTTGCTG TCGTTTCTAG AGATGGTGAA GCGGCCGTTC ACGCTGTCTG        60

GGTAGTAGGT GTTGTCGCCG CTGATGCTGA TGCTGG                                 96
```

( 2 ) INFORMATION FOR SEQ ID NO: 61:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO: 61:

Gly Phe Thr Phe Ser Ala Ser Ala Met Ser
                  5                  10

( 2 ) INFORMATION FOR SEQ ID NO: 62:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 62:

Trp Lys Tyr Glu Asn Gly Asn Asp Lys His Tyr Ala Asp Ser Val Asn
                  5                  10                  15

( 2 ) INFORMATION FOR SEQ ID NO: 63:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO: 63:

Asp Ala Gly Pro Tyr Val Ser Pro Thr Phe Phe Ala His
                  5                  10

( 2 ) INFORMATION FOR SEQ ID NO: 64:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO: 64:

Gly Phe Ser Phe Arg Ser Tyr Trp Met Thr
                  5                  10

( 2 ) INFORMATION FOR SEQ ID NO: 65:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO: 65:

Ser Ile Ser Ile Ser Gly Asp Asn Thr Tyr Tyr Pro Asp Ser Val Arg
                  5                  10                  15

( 2 ) INFORMATION FOR SEQ ID NO: 66:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO: 66:

Asp Pro Tyr Tyr Phe Ser Gly His Tyr Phe Asp Phe
                  5                  10

( 2 ) INFORMATION FOR SEQ ID NO: 67:

( i ) SEQUENCE CHARACTERISTICS:

```
            ( A ) LENGTH: 10 amino acids
            ( B ) TYPE: amino acid
            ( C ) STRANDEDNESS: single
            ( D ) TOPOLOGY: linear ( x i ) SEQUENCE DESCRIPTION: SEQ ID NO: 67:

Gly  Phe  Ser  Phe  Arg  Ser  Tyr  Ala  Met  Ser
                    5                        1 0

( 2 ) INFORMATION FOR SEQ ID NO: 68:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( x i ) SEQUENCE DESCRIPTION: SEQ ID NO: 68:

Gly  Phe  Thr  Phe  Ser  Ser  Tyr  Trp  Met  Thr
                    5                        1 0

( 2 ) INFORMATION FOR SEQ ID NO: 69:

( i ) SEQUENCE CHARACTERISTICS:
            ( A ) LENGTH: 16 amino acids
            ( B ) TYPE: amino acid
            ( C ) STRANDEDNESS: single
            ( D ) TOPOLOGY: linear ( x i ) SEQUENCE DESCRIPTION: SEQ ID NO: 69:

Ser  Ile  Ser  Ile  Ser  Gly  Asp  Asn  Thr  Tyr  Tyr  Pro  Asp  Ser  Val  Asn
                    5                        1 0                       1 5
```

HUMANIZED MONOCLONAL ANTIBODIES AGAINST HUMAN INTERLEUKIN-4

This application is a national phase of PCT/US93/01301, filed Feb. 18, 1993, which is a continuation in part of Ser. No. 07/841,659, filed Feb. 19, 1992, now abandoned.

BACKGROUND OF THE INVENTION

Human interleukin-4 (IL-4) was first cloned and characterized by Yokota et al. [Proc. Natl. Acad. Sci. 83:5894 (1986)]. IL-4 is a highly pleiotropic lymphokine which affects many different components of the immune system. It has T cell growth factor (TCGF) activity, and B cell growth factor activity. It is capable of potentiating the TCGF activity of interleukin-2 (IL-2) and the colony-forming activity of granulocyte-macrophage colony stimulating factor (GM-CSF).

It induces the preferential production of $IgG_1$ and IgE, induces the low affinity receptor for IgE (CD23), and induces the expression of human leukocyte class II DR antigens.

These activities suggest several possible therapeutic uses for IL-4, e.g., as an anti-tumor agent [Tepper et al., Cell 57:503 (1989)], a potentiating agent for IL-2 anticancer therapy, as a potentiating agent for GM-CSF-stimulated bone marrow regeneration, or as an agent to treat bare lymphocyte syndrome [Touraine, Lancet, pgs. 319–321 (Feb. 7, 1981); Touraine et al., Human Immunology 2:147 (1981); and Sullivan et al., J. Clin. Invest. 76:75 (1985)]. IL-4 and IL-4 agonists are thus potentially useful therapeutic agents.

The IgE- and CD23-inducing activity of IL-4 could have important consequences for persons suffering from allergic diseases. The availability of IL-4 antagonists could provide an alternative to the use of glucocorticoid steroids, which have many deleterious side effects, especially with prolonged usage [Goodman and Gillman, The Pharmacological Basis of Therapeutics, 6th Ed. (MacMillan Publishing Company, New York, 1980)].

Strongly blocking monoclonal antibodies specific for human IL-4 provide a means for constructing agonists or antagonists by generating anti-idiotype antibodies (U.S. Pat. No. 4,731,237) or by mimotope screening [Geysen et al., J. Immunol. Meth. 102:259 (1987); PCT patent applications WO 86/00991 and WO 86/06487]. Because most monoclonal antibodies are of rodent cell origin, however, there is a possibility that they would be immunogenic if used therapeutically in a human being, particularly if used over a long period of time. To avoid this possibility, it would be desirable to have human antibodies, or "humanized" antibodies, against human IL-4.

Initial efforts to reduce the immunogenicity of rodent antibodies involved the production of chimeric antibodies, in which mouse variable regions were fused with human constant regions [Liu et al., Proc. Natl. Acad. Sci. USA 84:3439 (1987)]. It has been shown, however, that mice injected with hybrids of human variable regions and mouse constant regions develop a strong anti-antibody response directed against the human variable region. This suggests that in the human system, retention of the entire rodent Fv region in such chimeric antibodies may still give rise to human anti-mouse antibodies.

It is generally believed that CDR loops of variable domains comprise the binding site of antibody molecules, the grafting of rodent CDR loops onto human frameworks (i.e., humanization) was attempted to further minimize rodent sequences [Jones et al., Nature 321:522 (1986); Verhoeyen et al., Science 239:1534 (1988)]. Studies by Kabat et al. [J. Immunol. 147:1709 (1991)] have shown that framework residues of antibody variable domains are involved in CDR loop support.

It has also been found that changes in framework support residues in humanized antibodies may be required to preserve antigen binding affinity. The use of CDR grafting and framework residue preservation in a number of humanized antibody constructs has been reported, e.g., by Queen et al. [Proc. Natl. Acad. Sci. USA 86:10029 (1989)], Gorman et al. [Proc. Natl. Acad. Sci. USA 88:4181 (1991)] and Hodgson [Bio/Technology 9:421 (1991)]. Exact sequence information has been reported for only a few humanized constructs.

From the foregoing, it is evident that there is a need for monoclonal antibodies specific for IL-4 that can be used therapeutically. Preferably, these antibodies should be humanized antibodies.

SUMMARY OF THE INVENTION

The present invention fills this need by providing monoclonal antibodies and compositions that are useful for the treatment of IL-4-related diseases, and intermediates for making such materials.

More particularly, this invention provides a monoclonal antibody produced by a hybridoma having the identifying characteristics of a cell line deposited under American Type Culture Collection Accession No. ATCC HB 9809, and the hybridoma itself.

This invention further provides polypeptides comprising heavy or light chain variable regions of a monoclonal antibody which have amino acid sequences defined by SEQ ID NO: 1, SEQ ID NO: 2, or subsequences thereof.

The present invention still further provides isolated DNAs which encode heavy or light chain variable regions of a monoclonal antibody which specifically binds to human interleukin-4 or complementarity determining regions (CDRs) of such antibody, or functional equivalents thereof.

This invention still further provides binding compositions, single-chain binding proteins, and chimeric or humanized monoclonal antibodies comprising CDRs from the light and/or heavy chain variable regions of the abovementioned monoclonal antibody.

Pharmaceutical compositions comprising a human IL-4 antagonist selected from the group consisting of a monoclonal antibody produced by a hybridoma having the identifying characteristics of a cell line deposited under American Type Culture Collection Accession No. ATCC HB 9809, a binding composition which specifically binds to human interleukin-4 comprising a heavy chain variable region and a light chain variable region from the monoclonal antibody produced by the hybridoma, a single-chain binding protein which specifically binds to human interleukin-4 comprising CDRs from the light and/or heavy chain variable regions of the monoclonal antibody produced by the hybridoma, a chimeric monoclonal antibody which specifically binds to human interleukin-4 comprising the heavy and light chain variable regions of the monoclonal antibody produced by the hybridoma, and a humanized monoclonal antibody which specifically binds to human interleukin-4 comprising CDRs from the heavy and light chain variable regions of the monoclonal antibody produced by the hybridoma; and a physiologically acceptable carrier, are also provided by this invention.

BRIEF DESCRIPTION OF THE FIGURES

This invention can be more readily understood by reference to the accompanying Figures, in which:

FIG. 2 illustrates the 215 nm absorption profile in the final purification step of human IL-4.

FIG. 6 shows amino acid residue replacements made in various humanized antibodies, compared to antibodies 25D2 and LAY.

DESCRIPTION OF THE INVENTION

Figure 1:
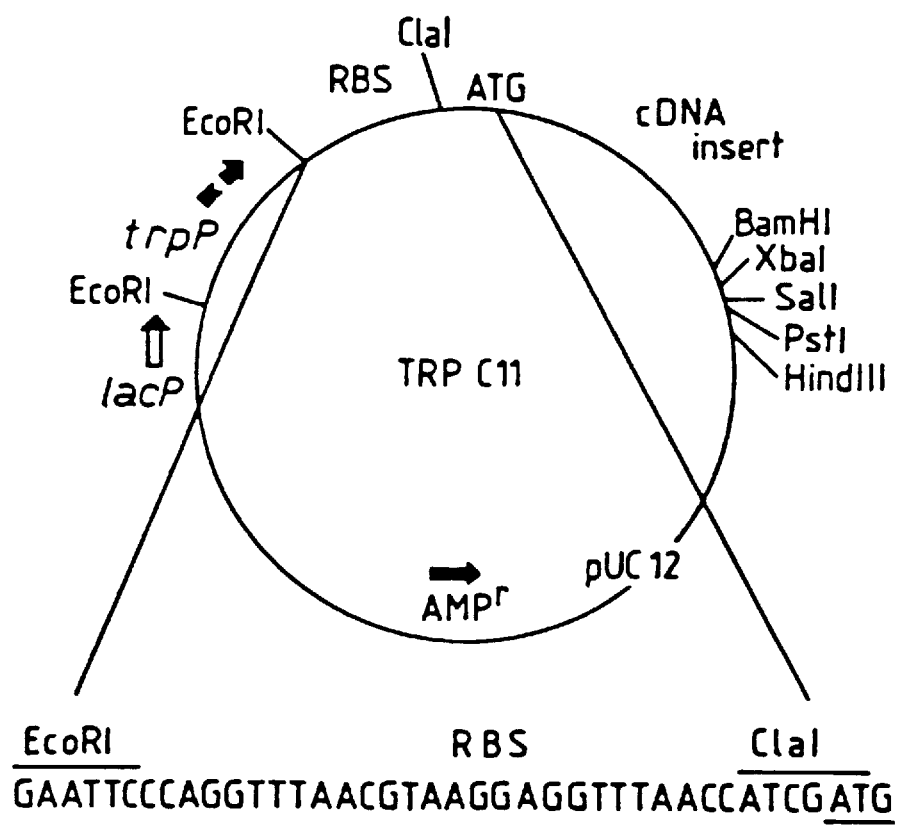
FIG. 1 is a schematic representation of an expression vector suitable for expressing unglycosylated human IL-4 in a bacterial host.

All references cited herein are hereby incorporated in their entirety by reference.

As used herein, the terms "DNA" and "DNAs" are defined as molecules comprising deoxyribonucleotides linked in standard 5' to 3' phosphodiester linkage, including both smaller oligodeoxyribonucleotides and larger deoxyribonucleic acids.

Antibodies comprise an assembly of polypeptide chains linked together by disulfide bridges. Two principal polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three or four different constant regions, and light chains comprise a single variable region (different from that of the heavy chain) and a single constant region (different from those of the heavy chain). The variable regions of the heavy chain and light chain are responsible for the antibody's binding specificity.

As used herein, the term "CDR structural loops" means the three light chain and the three heavy chain regions in the variable portion of an antibody that bridge β strands on the binding portion of the molecule. These loops have characteristic canonical structures [Chothia et al., *J. Mol. Biol.* 196:901 (1987); Chothia et al., *J. Mol. Biol.* 227:799 (1992)].

The term "Kabat CDRs" refers to hypervariable antibody sequences on heavy and light chains as defined by Kabat et al. [*Sequences of Proteins of Immunological Interest*, 4th Edition, 1987, U.S. Department of Health and Human Services, National Institutes of Health].

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

The terms Fab, Fc, F(ab)$_2$, and Fv are employed with their standard immunological meanings [Klein, *Immunology* (John Wiley, New York, 1982); Parham, Chapter 14, in Weir, ed. *Immunochemistry*, 4th Ed. (Blackwell Scientific Publishers, Oxford, 1986)].

As used herein the term "monoclonal antibody" refers to a homogeneous population of immunoglobulins which are capable of specifically binding to human IL-4. It is understood that human IL-4 may have one or more antigenic determinants comprising (1) peptide antigenic determinants which consist of single peptide chains within human IL-4, (2) conformational antigenic determinants which consist of more than one spatially contiguous peptide chains whose respective amino acid sequences are located disjointly along the human IL-4 polypeptide sequence; and (3) post-translational antigenic determinants which consist, either in whole or part, of molecular structures covalently attached to human IL-4 after translation, such as carbohydrate groups, or the like. The antibodies of the invention may be directed against one or more of these determinants.

As used herein the term "binding composition" means a composition comprising two polypeptide chains (1) which, when operationally associated, assume a conformation having high binding affinity for human IL-4, and (2) which are derived from a hybridoma producing monoclonal antibodies specific for human IL-4. The term "operationally associated" is meant to indicate that the two polypeptide chains can be positioned relative to one another for binding by a variety of means, including association in a native antibody fragment, such as Fab or Fv, or by way of genetically engineered cysteine-containing peptide linkers at the carboxyl termini.

Hybridomas of the invention are produced by well-known techniques. Usually, the process involves the fusion of an immortalizing cell line with a B-lymphocyte that produces the desired antibody. Alternatively, non-fusion techniques for generating immortal antibody-producing cell lines are possible, and come within the purview of the present invention, e.g., virally-induced transformation [Casali et al., Science 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining the appropriate lymphocytes from mammals injected with the target antigen are well known. Generally, peripheral blood lymphocytes (PBLs) are used if cells of human origin are desired, or spleen cells or lymph node cells are used if non-human mammalian sources are desired. A host mammal is injected with repeated dosages of the purified antigen, and the mammal is permitted to generate the desired antibody-producing cells before these are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. From among these hybridomas, those secreting the desired antibody are selected by assaying their culture medium by standard immunoassays, such as Western blotting, ELISA (enzyme-linked immunosorbent assay), RIA (radioimmunoassay), or the like. Antibodies are recovered from the medium using standard protein purification techniques [Tijssen, *Practice and Theory of Enzyme Immunoassays* (Elsevier, Amsterdam, 1985)]. Many references are available for guidance in applying any of the above techniques [Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)].

Monoclonal antibodies can also be produced using well known phage library systems.

The use and generation of fragments of antibodies is also well known, e.g., Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Moreover, such compounds and compositions of the invention can be used to construct bi-specific antibodies by known techniques, e.g., by further fusions of hybridomas (i.e. to form so-called quadromas; Reading, U.S. Pat. No. 4,474,493) or by chemical reassociation of half molecules [Brennan et al., Science 229:81 (1985)].

Hybridomas and monoclonal antibodies of the invention are produced against either glycosylated or unglycosylated versions of recombinantly-produced mature human IL-4. Generally, unglycosylated versions of human IL-4 are produced in *E. coli*, and glycosylated versions are produced in mammalian cell hosts, e.g., CV1 or COS monkey cells, mouse L cells, or the like. Recombinantly-produced mature human IL-4 is produced by introducing an expression vector into a host cell using standard protocols [Maniatis et al., *Molecular Cloning: A Laboratory Manual* (Cold Spring Harbor Laboratory, New York, 1982); Okayama and Berg, Mol. Cell. Biol. 2:161 (1982); Okayama and Berg, Mol. Cell. Biol. 3:280 (1983); Hamer, Genetic Engineering 2:83 (1980); U.S. Pat. No. 4,599,308; Kaufman et al., Mol. Cell. Biol. 2:1304 (1982)].

Construction of bacterial or mammalian expression vectors is well known in the art, once the nucleotide sequence encoding a desired protein is known or otherwise available. For example, DeBoer (U.S. Pat. No. 4,511,433) has disclosed promoters for use in bacterial expression vectors. Goeddel et al. (U.S. Pat. No. 4,601,980) and Riggs (U.S. Pat. No. 4,431,739) have disclosed the production of mammalian proteins by *E. coli* expression systems. Riggs (supra), Ferretti et al. [Proc. Natl. Acad. Sci. 83:599 (1986)], Sproat et al. [Nucleic Acids Res. 13:2959 (1985)] and Mullenbach et al. [J. Biol. Chem. 261:719 (1986)] disclose how to construct synthetic genes for expression in bacteria.

The amino acid sequence of mature human IL-4 has been disclosed by Yokota et al. (supra), and cDNA encoding human IL-4 carried by the pcD vector described by Yokota et al. has been deposited with the American Type Culture Collection (ATCC), Rockville, Md., under accession number ATCC 67029.

Many bacterial expression vectors and hosts are available commercially or through the ATCC. Preferably, human IL-4 for immunizing host animals is isolated from culture supernatants of COS, CV1, or mouse L cells which have been transiently transfected by the above-mentioned pcD vector. Recombinant human IL-4 can also be purchased, e.g., from Genzyme Corporation (Boston, Mass.) and from ICN Flow (Costa Mesa, Calif.).

In particular, such techniques can be used to produce interspecific monoclonal antibodies, wherein the binding region of one species is combined with a non-binding region of the antibody of another species [Liu et al., Proc. Natl. Acad. Sci. USA 84:3439 (1987)]. For example, the CDRs from a rodent monoclonal antibody can be grafted onto a human antibody, thereby "humanizing" the rodent antibody [Riechmann et al., Nature 332:323 (1988)]. More particularly, the CDRs can be grafted into a human antibody variable region with or without human constant regions. Such methodology has been used to humanize a mouse monoclonal antibody against the p55 (Tac) subunit of the human interleukin-2 receptor [Queen et al., Proc. Natl. Acad. Sci. USA 86:10029 (1989)].

Messenger RNA (mRNA) extracted from the hybridoma of the invention is useful for cloning and expressing fragments of the monoclonal antibody in bacteria, yeast, or other hosts. Complementary DNAs (cDNAs) produced from such mRNA which encode the heavy and light chain variable regions and CDRs of such monoclonal antibodies can be used to produce engineered antibodies and single-chain binding proteins by standard methods.

The location of the CDRs within the variable regions of the antibodies can be determined using a number of well known standard methods. For example, Kabat et al. [*Sequences of Proteins of Immunological Interest*, 4th Edition, 1987, U.S. Department of Health and Human Services, National Institutes of Health] have published rules for locating CDRs. CDRs determined using these rules are referred to herein as "Kabat CDRs." Computer programs are also available which can be used to identify CDR structural loops on the basis of the amino acid residues involved in the three-dimensional binding site loops of the antibody chains, e.g., as described below.

The humanized antibodies described below were produced using a two-step method which involved (a) selecting human antibody sequences that were to be used as human frameworks for humanization, and (b) determining which variable region residues of the rodent monoclonal antibody should be selected for insertion into the human framework chosen.

The first step involved selection of the best available human framework sequences for which sequence information was available. This selection process was based upon the following selection criteria:

(1) Percent Identities

The sequences of the heavy and light chain variable regions of the rodent monoclonal antibody that was to be humanized were optimally aligned and compared with other known human antibody heavy and light chain variable region sequences. This is in contrast to the methods of the prior art, which rely heavily on the use of only two human antibodies, NEW and KOL. Structural information is available for these antibodies, the designations for which are the initials of human patients from which they were derived. The structure of antibody HIL is also known now (Brookhaven Code P8FAB).

Once the sequences were thus compared, residue identities were noted and percent identities are determined. All other factors being equal, it is desirable to select a human antibody which has the highest percent identity with the animal antibody.

(2) Sequence Ambiguities

The known human antibody chain sequences were then evaluated for the presence of unidentified residues and/or ambiguities, which are sequence uncertainties. The most common of such uncertainties are mistaken identification of an acidic amino acid for an amide amino acid due to loss of ammonia during the sequencing procedure, e.g., incorrect identification of a glutamic acid residue, when the residue actually present in the protein was a glutamine residue. Uncertainties are identified by examination of data bases such as that of Kabat et al., supra. All other factors being equal, it is desirable to select a human antibody chain having as few such ambiguities as possible.

(3) Pin-region Spacing

Antibody chain variable regions contain intra-domain disulfide bridges. The distance (number of residues) between the cysteine residues comprising these bridges is referred to as the Pin-region spacing [Chothia et al., J. Mol. Biol. 196:901 (1987)]. All other factors being equal, it is most desirable that the Pin-region spacing of a human antibody selected be similar or identical to that of the animal antibody. It is also desirable that the human sequence Pin-region spacing be similar to that of a known antibody 3-dimensional structure, to facilitate computer modeling.

Based upon the foregoing criteria, the human antibody having the best overall combination of desirable characteristics, the antibody LAY, was selected as the framework for humanization of the rodent antibody.

The second step involved determination of which of the rodent antibody variable region sequences should be selected for grafting into the human framework. This selection process was based upon the following selection criteria:

(1) Residue Selection

Two types of potential variable region residues were evaluated in the rodent antibody sequences, the first of which were called "minimal residues." These minimal residues comprised CDR structural loops plus any additional residues required, as shown by computer modeling, to support and/or orient the CDR structural loops.

The other type of potential variable region residues were referred to as "maximal residues." They comprised the minimal residues plus Kabat CDRs plus any additional residues which, as determined by computer modeling, fell within about 5 Å of CDR structural loop residues and possessed a water solvent accessible surface [Lee et al., J. Biol. Chem. 55:379 (1971)] of about 5 Å$^2$ or greater.

(2) Computer Modeling

To identify potential variable region residues, computer modeling was carried out on (a) the variable region sequences of the rodent antibody that was to be humanized, (b) the selected human antibody framework sequences, and (c) all possible recombinant antibodies comprising the human antibody framework sequences into which the various minimal and maximal animal antibody residues had been grafted.

The computer modeling was performed using software suitable for protein modeling and structural information obtained from an antibody that (a) had variable region amino acid sequences most nearly identical to those of the rodent antibody and (b) had a known 3-dimensional structure. The software used was the SYBYL Biopolymer Module software (Tripos Associates).

Based upon results obtained in the foregoing analysis, recombinant chains containing the rodent variable regions producing a computer modeling structure most nearly approximating that of the rodent antibody were selected for humanization.

The nucleotide sequences of cDNAs encoding the heavy (V$_H$) and light (V$_L$) chain variable regions of anti-human IL-4 monoclonal antibody 25D2, the production of which is described below, are defined in the Sequence Listing by SEQ ID NOs:1 and 2, respectively. The amino acid sequences predicted from these nucleotide sequences are also defined in SEQ ID NOs: 1 and 2.

The CDRs of the heavy chain variable region of monoclonal antibody 25D2 as determined by the method of Kabat et al., supra, comprise amino acid residues 31–35, 50–66 and 99–110 of the amino acid sequence defined by SEQ ID NO:1. As determined by computer analysis of binding site loop structures as described below, the CDRs of the heavy chain variable region of monoclonal antibody 25D2 comprise amino acid residues 26–32, 53–56 and 100–108 of the amino acid sequence defined by SEQ ID NO: 1.

Nucleotide sequences encoding the foregoing heavy chain CDRs comprise bases 91–105, 148–198 and 295–330 (Kabat determination) and bases 76–96, 157–168 and 298–324 (loop analysis) of the nucleotide sequence defined by SEQ ID NO: 1.

The CDRs of the light chain variable region of monoclonal antibody 25D2 as determined by the method of Kabat et al., supra, comprise amino acid residues 24–34, 50–56 and 89–96 of the amino acid sequence defined by SEQ ID NO: 2. As determined by computer analysis of binding site loop structures as described below, the CDRs of the light chain variable region of monoclonal antibody 25D2 comprise amino acid residues 26–31, 50–52 and 91–95 of the amino acid sequence defined by SEQ ID NO: 2.

Nucleotide sequences encoding the foregoing light chain CDRs comprise bases 70–102, 148–168 and 265–288 (Kabat determination) and bases 76–93, 148–156 and 271–285 (loop analysis) of the nucleotide sequence defined by SEQ ID NO: 2.

From the foregoing, it can be seen that the CDRs thus determined are encoded by from 9 to 51 bases. Useful DNAs for protein engineering therefore comprise from about 12 to 363 bases and from about 9 to 321 bases of the nucleotide sequences defined by SEQ ID NOs: 1 and 2, respectively. Also of importance is the constant region for selection of isotype for protein engineering.

If the CDRs of the invention are used to produce humanized antibodies by grafting onto a human antibody, it may be desirable to include one or more amino acid residues which, while outside the CDRs, are likely to interact with the CDRs or IL-4 (Queen et al., supra).

The CDRs of the invention can also form the basis for the design of non-peptide mimetic compounds which mimic the functional properties of antibody 25D2. Methods for producing such mimetic compounds have been described by Saragovi et al. [Science 253:792 (1991)].

In addition to providing a basis for antibody humanization, the information in SEQ ID NOs:1 and 2 can be used to produce single-chain IL-4 binding proteins comprising linked heavy and light chain fragments of the Fv region, as described by Bird et al. [Science 242:423 (1988)], or biosynthetic antibody binding sites (BABS), as described by Huston et al. [Proc. Natl. Acad. Sci. USA 85:5879 (1988)]. Single-domain antibodies comprising isolated heavy-chain variable domains [Ward et al., Nature 341:544 (1989)] can also be prepared using the information in SEQ ID NO:1.

Two or more CDRs of the invention can also be coupled together in a polypeptide, either directly or by a linker sequence. One or more of the CDRs can also be engineered into another (non-immunoglobulin) polypeptide or protein, thereby conferring IL-4 binding capability on the polypeptide or protein.

Polypeptides "comprising a heavy or light chain variable region of a monoclonal antibody having a sequence defined by SEQ ID NOs: 1 or 2, or a subsequence thereof", are defined herein to include all of the foregoing CDR-containing embodiments.

DNAs which encode the heavy and light chain variable regions of antibody 25D2 or the CDRs therefrom can be prepared by standard methods using the nucleic acid sequence information provided in SEQ ID NOs: 1 and 2. For example, such DNA can be chemically synthesized using, e.g., the phosphoramidite solid support method of Matteucci et al. [J. Am. Chem. Soc. 103:3185 (1981)], the method of Yoo et al. [J. Biol. Chem. 764:17078 (1989)], or other well known methods.

Alternatively, since the sequence of the gene and the site specificities of the many available restriction endonucleases are known, one skilled in the art can readily identify and isolate the gene from the genomic DNA of hybridoma MP4.25D2.11 and cleave the DNA to obtain the desired sequences. The PCR method [Saiki et al., Science 239:487 (1988)], as exemplified by Daugherty et al. [Nucleic Acids Res. 19:2471 (1991)] can also be used to obtain the same result. Primers used for PCR can if desired be designed to introduce appropriate new restriction sites, to facilitate incorporation into a given vector.

Still another method for obtaining DNAs encoding the heavy and light chain variable regions of antibody 25D2 entails the preparation of cDNA, using mRNA isolated from hybridoma IC1.11B4.6 or MP4.25D2.11 as a template, and the cloning of the variable regions therefrom using standard methods [see, e.g., Wall et al., Nucleic Acids Res. 5:3113 (1978); Zalsut et al., Nucleic Acids Res. 8:3591 (1980); Cabilly et al., Proc. Natl. Acad. Sci. USA 81:3273 (1984); Boss et al., Nucleic Acids Res. 12:3791 (1984); Amster et al., Nucleic Acids Res. 8:2055 (1980); Moore et al., U.S. Pat. No. 4,642,234].

Of course, due to the degeneracy of the genetic code, many different nucleotide sequences can encode polypeptides having the amino acid sequences defined by SEQ ID NOs: 1 and 2 and the CDRs therein. The codons can be selected for optimal expression in prokaryotic or eukaryotic systems. Such functional equivalents are also a part of this invention. Moreover, those skilled in the art are aware that there can be conservatively modified variants of polypeptides and proteins in which there are minor amino acid substitutions, additions or deletions that do not substantially alter biological function [Anfinsen, Science 181:223 (1973); Grantham, Science 185:862 (1974)].

Such conservatively modified variants of the amino acid sequences defined by SEQ ID NOs: 1 and 2 are also contemplated by this invention. It is well within the skill of the art, e.g., by chemical synthesis or by the use of modified PCR primers or site-directed mutagenesis, to modify the DNAs of this invention to make such variants if desired.

It may also be advantageous to make more substantial modifications. For example, Roberts et al. [Nature 328:731 (1987)] have produced an antibody with enhanced affinity and specificity by removing two charged residues at the periphery of the combining site by site-directed mutagenesis.

Insertion of the DNAs encoding the heavy and light chain variable regions of antibody 25D2 into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

Pharmaceutical compositions can be prepared using the monoclonal antibodies, binding compositions or single-chain binding proteins of the invention, or anti-idiotypic antibodies prepared against such monoclonal antibodies, to treat IL-4-related diseases.

Some of the compositions have IL-4 blocking or antagonistic effects and can be used to suppress IL-4 activity. Such compositions comprise the monoclonal antibodies, binding compositions or single-chain binding proteins of the invention and a physiologically acceptable carrier.

Other compositions comprise anti-idiotypic antibodies prepared using the monoclonal antibodies of the invention as an antigen and a physiologically acceptable carrier. These anti-idiotypic antibodies, which can be either monoclonal or polyclonal and are made by standard methods, may mimic the binding activity of IL-4 itself. Thus, they may potentially be useful as IL-4 agonists or antagonists.

Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. Remington's Pharmaceutical Science, 15th Ed. (Mack Publishing Company, Easton, Pa., 1980). Alternatively, compositions of the invention may be introduced into a patient's body by implantable drug delivery systems [Urquhart et al., Ann. Rev. Pharmacol. Toxicol. 24:199 (1984)].

EXAMPLES

The following non-limiting Examples will serve to illustrate the present invention. Selection of vectors and hosts as well as the concentration of reagents, temperatures, and the values of other variables are only to exemplify application of the present invention and are not to be considered limitations thereof.

Unless otherwise indicated, percentages given below for solids in solid mixtures, liquids in liquids, and solids in liquids are on a wt/wt, vol/vol and wt/vol basis, respectively. Sterile conditions were maintained during cell culture.

Example I

Production of Glycosylated Human IL-4 by Transfection of COS 7 Monkey Cells with pcD-human-IL-4

The expression vector pcD-human-IL-4 and host COS 7 cells are available from the American Type Culture Collection under accession numbers 67029 and CRL 1651, respectively. The pcD-human-IL-4 clone was amplified, the plasmid DNA was purified, and then a standard transfection protocol was used to transfect COS 7: About $1 \times 10^6$ COS 7 cells are seeded onto 100 mm tissue culture plates containing Dulbecco's Modified Eagle's medium (DME), 10% fetal calf serum, and 4 mM L-glutamine. About 24 hours after seeding, the medium is aspirated from the plates and the cells are washed twice with serum free buffered (50 mM Tris) DME. To each plate is added 4 ml serum free buffered DME (with 4 mM L-glutamine), 80 microliters DEAE-dextran, and 5 micrograms of pcD-human-IL-4 DNA. The cells are incubated in this mixture for 4 hours at 30° C., after which the mixture is aspirated off and the cells are washed once with serum free buffered DME. After washing, 5 ml of DME with 4 mM L-gutamine, 100 μM chloroquine, and 2% fetal calf serum is added to each plate, and the cells are incubated for 3 hours, and then twice washed with serum free buffered DME. Next, 5 ml DME with 4 mM L-glutamine and 4% fetal calf serum is added and the cells are incubated at 37° C. for 24 hours. Afterwards the cells are washed 1–3 times with DME or PBS, 5 ml serum free DME (with 4mM L-glutamine) is added, and the cells are incubated at 37° C. until culture supernatants are harvested 5 days later.

Example II

Purification of Glycosylated Human IL-4 from COS 7 Transfection Supernatants

Biological Assay for Purification.

T cell growth factor (TCGF) activity was used to assay human IL-4 during purification from the supernatants produced according to Example I. Several standard assays have been described for TCGF activity [Devos et al., Nucleic Acids Res. 11:4307 (1983); Thurman et al., J. Biol. Response Modifiers 5:85 (1986); Robert-Guroff et al., Chapter 9 in Guroff, Ed. *Growth and Maturation Factors* (John Wiley, New York, 1984)]. Generally, the TCGF assays are based on the ability of a factor to promote the proliferation of peripheral T lymphocytes or IL-2-dependent T cell lines [Gillis et al. J. Immunol. 120:2027 (1978)]. Proliferation can be determined by standard techniques, e.g. tritiated thymidine incorporation, or by colorimetric methods [Mosmann, J. Immunol. Meth. 65:55 (1983)].

The assay for human IL-4 TCGF activity was carried out as follows: Blood from a healthy donor was drawn into a heparinized tube and layered onto Ficoll-Hypaque; e.g., 5 ml of blood per 3 ml Ficoll-Hypaque in a 15 ml centrifuge tube. After centrifugation at 3000×g for 20 minutes, cells at the interface were aspirated and diluted in a growth medium consisting of RPMI 1640 containing 10% fetal calf serum, 50 μM 2-mercaptoethanol, 20 μg/ml phytohemagglutinin (PHA), and recombinant human IL-2. After 5–10 days of incubation at 37° C., the PHA-stimulated peripheral blood lymphocytes (PBLs) were washed and used in 2 day calorimetric assays (Mossman, supra). Serial two-fold dilutions of an IL-4 standard (supernatants from pcD-human-IL4-transfected COS 7 cells) or the fraction to be tested were performed in 96-well trays utilizing the growth medium described above to yield a final volume of 50 μl/well. 50 μl of the PHA-stimulated PBLs at about 4–8×10$^6$ cells/ml were added to each well and the trays were incubated at 37° C. for 2 days. Cell growth was then measured according to Mosmann (supra).

One unit, as used herein, is the amount of factor which in one well (0.1 ml) stimulates 50% maximal proliferation of 2×10$^4$ PHA-stimulated PBLs over a 48 hour period.

Purification

Purification was accomplished by a sequential application of cation exchange chromatography, gel filtration and reverse-phase high pressure liquid chromatography. All operations were performed at 4° C.

The COS-7 cells were removed by centrifugation, and the supernatant was concentrated about 10-fold by ultrafiltration and stored at −80° C. until further processed. IL-4 titers were determined by assaying for the ability of the protein to stimulate proliferation of phytohemagglutinin-induced human peripheral blood lymphocytes, i.e. by TCGF activity using the standard assay described above.

Concentrated COS-7 supernatant, having TCGF activity of about 10$^4$–10$^6$ units/ml and a protein content of about 15–20 mg/ml, was dialyzed against two changes of 50 mM sodium HEPES, pH 7.0 over a 24 hour period (each change being approximately 10–15 times the volume of one concentrate). The dialysate was applied to a column (1×2.5 cm) of S-SEPHAROSE® (flow rate: 0.2 ml/min) pre-equilibrated with 50 mM sodium HEPES, pH 7.0. The column was washed with 15 column volumes of equilibrating buffer and then eluted with 20 column volumes of a linear sodium chloride gradient extending from 0 to 0.5M sodium chloride in 50 mM sodium HEPES, pH 7.0. The elution was terminated isocratically with 5 column volumes of 50 mM sodium HEPES, 0.5M NaCl, pH 7.0. 1.5 ml and 1.8 ml fractions were collected from two separate batches. IL-4 titers were found for both chromatographies to elute between 300 mM and 500 mM sodium chloride.

The fractions from the S-SEPHAROSE® columns containing IL-4 titers were combined for total separate volumes of 9.0 and 10.8 ml. Both volumes were concentrated to 1.9 ml by ultrafiltration using an Amicon YM5 membrane (molecular weight cut-off: 5000). The recovery of protein from this step was about 80%. The concentrated IL-4 solution was applied to a SEPHADEX G-100® column (1.1×58 cm) pre-equilibrated in 50 mM HEPES, 0.4M NaCl, pH 7.0, and the column was eluted with the same buffer at 0.15 ml/min. A total of 50 fractions (1.0 ml/fraction) was collected and analyzed for IL-4 titers. A peak in biological activity was observed at an apparent molecular weight of 22,000 daltons. The SEPHADEX G-100® column was calibrated for apparent molecular determination with bovine serum albumin (65,000 daltons), carbonic anhydrase (30,000 daltons) and cytochrome C (11,700 daltons).

A fraction from the SEPHADEX G-100® column containing IL-4 activity was concentrated 3–4 fold in vacuo and was injected onto a VYDAC C-4® guard column (4.6×20 mm). A linear gradient of 0 to 72% (v/v) acetonitrile in 0.1% (v/v) trifluoroacetic acid (TFA) was produced in 15 minutes at a column temperature of 35° and a flow rate of 1.0 ml/min. Three peaks resulted that were detected at 214 nm with retention times of 7, 8.2 and 8.7 min. (peaks 1, 2, and 3 of FIG. 2, respectively). A 40 μl aliquot of peak 2 (8.2 min. elution time) was lyophilized and redissolved in minimal essential medium containing 10% fetal calf serum. This solution showed a positive TCGF response. A 300 μl aliquot of peak 2 was evaporated to dryness and redissolved in 200 μl of 0.1% (w/v) sodium dodecylsulfate sulfate (SDS). A 2 μl aliquot was diluted in 200 μl of 1% (v/v) TFA and rechromatographed. The HPLC of this sample demonstrated a single peak at 215 nm. Peak 2 material indicated an activity of about 7×10$^8$ units/mg.

Example III

Production of Unglycosylated Human IL-4 in *Escherichia coli*

An *E. coli* expression vector, denoted TRPC11, was constructed using standard techniques, e.g. as disclosed in Maniatis et al., *Molecular Cloning: A Laboratory Manual* (Cold Spring Harbor Laboratory, N.Y., 1982).

The TRPC11 vector was constructed by ligating a synthetic consensus RBS fragment to ClaI linkers (ATGCAT) and by cloning the resulting fragments into ClaI-restricted pMT11hc (which had been previously modified to contain the ClaI site). pMT11hc is a small (2.3 kilobase) high copy, AMP$^R$, TET$^S$ derivative of pBR322 that bears the EcoRI-HindIII polylinker region of the πVX plasmid (described by Maniatis et al., cited above). It was modified to contain the ClaI site by restricting pMT11hc with EcoRI and BamHI, filling in the resulting sticky ends and ligating with ClaI linker (CATCGATG), thereby restoring the EcoRI and BamHI sites and replacing the SmaI site with a ClaI site.

One transformant from the TRPC11 construction had a tandem RBS sequence flanked by ClaI sites. One of the ClaI sites and part of the second copy of the RBS sequence were removed by digesting this plasmid with PstI, treating with BalI nuclease, restricting with EcoRI, and treating with T4 DNA polymerase in the presence of all four deoxynucleotide triphosphates. The resulting 30–40 bp fragments were recovered by polyacrylamide gel electrophoresis and cloned into SmaI-restricted pUC12. A 248 bp *E. coli* trpP-bearing EcoRI fragment derived from pKC101[described by Nichols et al. in *Methods in Enzymology*, Vol. 101, pg. 155 (Academic Press, N.Y. 1983)] was then cloned into the EcoRI site to complete the TRPC11 construction, which is illustrated in FIG. 1.

TRPC11 was employed as a vector for human IL-4 cDNA by first digesting it with ClaI and BamHI, purifying it, and then mixing it with the EcoRV/BamHI fragment of pcD-125 (deposited with the ATCC under accession number 67029) in a standard ligation solution containing 0.1 micromolar of a double-stranded synthetic linker comprised of two oligonucleotides, the sequences of which are defined by SEQ ID NOs: 3 and 4.

*E. coli* AB1899 was transformed directly with the ligation solution using the standard calcium chloride procedure, propagated, and plated. Colonies containing the IL-4 cDNA insert were selected using a labeled oligonucleotide probe. The transformants were cultured in L-broth, and IL-4 was expressed constitutively.

Example IV

Purification of Unglycosylated Human IL-4 from Aggregates Produced by *Escherichia coli*

A 1 liter culture of *E. coli* AB1899 (lon⁻) (obtained from Yale University *E. coli* Genetics Center, New Haven, Conn.) was grown to $OD_{560}=2$ (about $1.6 \times 10^9$ cells/ml). Cells were harvested by centrifugation at 4500×g for 15 minutes at 4° C. The pellets were resuspended in 30 ml of 50 mM Tris buffer, pH 8.0, containing 50 mM NaCl, 1 mM ethylenediaminetetraacetic acid (EDTA), and 0.1 mM phenylmethylsulfenyl fluoride (PMSF). EDTA and PMSF were added to inhibit protease activity which might degrade the human IL-4 before purification. Next, the cells were sonicated [50 pulses (50%) at 70 watts] and centrifuged at 25,000×g for 15 minutes at 4° C. The major protein component of the resulting pellet was shown to be IL-4 by comparing the gel band pattern of electrophoretically separated pellet material (which had been solubilized in sodium dodecylsulphate (SDS) and stained with Coomassie Blue) with a negative control.

After removal of the supernatant, pellet material was resuspended in Tris buffer solution (50 mM Tris, 50 mM NaCl, 1 mM EDTA, 0.1 mM PMSF, pH 8.0; 9 ml for each gram of pellet material) containing 5M guanidine HCl, 2 mM glutathione (reduced form), and 0.2 mM glutathione (oxidized form). After approximately 1 hour at room temperature, the solution was diluted 1:9 into a Tris buffer solution, pH 8.0, containing 2 mM glutathione (reduced form) and 0.2 mM glutathione (oxidized form). Whenever precipitates formed during the dilution, dialysis, or concentration steps, they were removed by centrifugation before proceeding. The entire volume was then dialyzed overnight 3 times against 3 liters of phosphate buffer solution. The dialyzate (i.e. the material retained by the dialysis bag) was concentrated by an Amicon YM5 filter (final concentration 8 mg/ml), and subjected to gel filtration chromatography (column: P30 (BioRad), 1.5×90 cm; PBS elution buffer; flow rate: 8 ml/hr). Fractions were collected over 15 minute intervals. Fractions 23–27 were pooled and further analyzed by reverse phase HPLC. Such analysis indicated that the pooled factions contained >95% pure human IL-4. The yield from the 1 liter culture ($OD_{560}$ of 2) was 2 mg of human IL-4 with a specific activity of $5 \times 10^7$ units/mg.

Example V

Production of Hybridoma IC1.11B4.6

A male Lewis rat was immunized intraperitoneally (i.p.) with 1 ml of human IL-4 solution emulsified with 1 ml complete Freund's adjuvant (CFA). The human IL-4 solution consisted of human IL-4 at a concentration of 14 µg/ml in 10 mM Tris-HCl, 0.5M NaCl, pH 7.4. The human IL-4 was produced in accordance with Examples I and II, and had a specific activity of $2 \times 10^7$ units/mg. Two weeks after the initial immunization, the rat was again injected i.p. with 1 ml human IL-4 solution emulsified with 1 ml CFA. Three months after the second injection, the rat was boosted intravenously with 1 ml human IL-4 solution (15 µg). Four days after the booster injection the rat was sacrificed, blood was collected, and the spleen was removed for fusion.

Spleen cells were fused with mouse myeloma cells, P3X63-Ag8.653 (ATCC CRL 1580), in a 1:1 ratio using polyethylene glycol (PEG). The cell suspension ($3.5 \times 10^5$ cells/ml in HAT medium) was distributed into 40 96-well plates. Ten days later hybridoma supernatants were tested for their ability to bind to human IL-4 immobilized directly on microtiter plates (indirect ELISA), or to human IL-4 bound to immobilized polyclonal IgG fraction of rabbit anti-human IL-4. Bound antibody was detected by peroxidase-conjugated goat anti-rat immunoglobulin with a standard protocol.

Hybridomas secreting antibodies reacting with IL-4 were cloned by limiting dilution. IC1.11B4.6 was one such hybridoma selected by these procedures. Antibodies from IC1.11B4.6 were determined to be of the $IgG_{2a}$ isotype. The hybridoma can be stored (e.g., −70° C. in culture medium with 10% DMSO) and cultured using standard mammalian cell culture techniques (e.g., RPMI 1640 with 10% fetal bovine serum, supplemented with I mM glutamine and 50 mM 2-mercaptoethanol).

Example VI

Production of Hybridoma MP4.25D2.11

A collection of hybridomas was produced and their antibodies were screened for human IL-4 specificity in substantially the same manner as in Example V. The hybridomas of the collection were then screened further for the ability of their antibodies to block the TCGF activity of human IL-4 in a standard in vitro assay (as disclosed in Example II). Of several blocking monoclonals identified, that produced by MP4.25D2.11 was selected as having the highest titer of blocking activity. The antibodies produced by MP4.25D2.11 were determined to be rat $IgG_1$.

Example VII

Sandwich Assay for Human IL-4

100 µl of rabbit polyclonal anti-human IL-4 antibody (10 µg/ml in PBS purified on a protein A affinity column) is adsorbed onto the surface of each well in a 96-well polyvinyl chloride microtiter plate for 2 hrs. at 37° C. (PBS consists of 8.0 g of NaCl, 0.2 g of $KH_2PO_4$, 2.9 g of $Na_2HPO_4.12H_2O$, and 0.2 g of KCl, in 1 liter of distilled water. The pH is 7.4.) The plate is washed with PBS-Tween (prepared exactly as PBS, except that 0.5 ml of Tween 20 is added per liter) to remove unbound antibody, and then duplicate serial dilutions (in PBS) of purified *E. coli*-produced human IL-4 are placed in two 12-well rows of wells in order of decreasing IL-4 concentrations, which range from 1000 pg/ml to 15 pg/ml. The following samples were loaded into the remaining wells: (1) culture supernatants from a human T cell clone, e.g., ClLy1$^+$2$^-$/9 (ATCC CRL 8179), (2) culture supernatants of COS 7 cells transfected with pcD- human-IL-4, (3) human serum containing different concentrations of purified COS7-produced IL-4, and (4) samples containing human IL-1α, IL-2, IL-3, IFN-γ, IFN-α2b, GM-CSF, and BSF-2.

All of the samples were incubated for 2 hours at room temperature. After washing with PBS-Tween, a 1:10 dilution of supernatant from a culture of IC1.11B4.6 was added to each well (100) 1/well) and was allowed to incubate for 1 hour at room temperature. After incubation, the plate was washed and peroxidase-conjugated goat anti-rat antibody was added and allowed to incubate for 1 hour at room temperature, after which the plate was washed. Next, the peroxidase substrate ABTS was added, and the human IL-4 concentrations were determined by means of optical densities in the wells. The results indicate that the assay can detect mammalian-produced human IL-4 at concentrations as low as 50 pg/ml in human serum, and that the assay does not detect any of the lymphokines listed above.

Figure 3A:
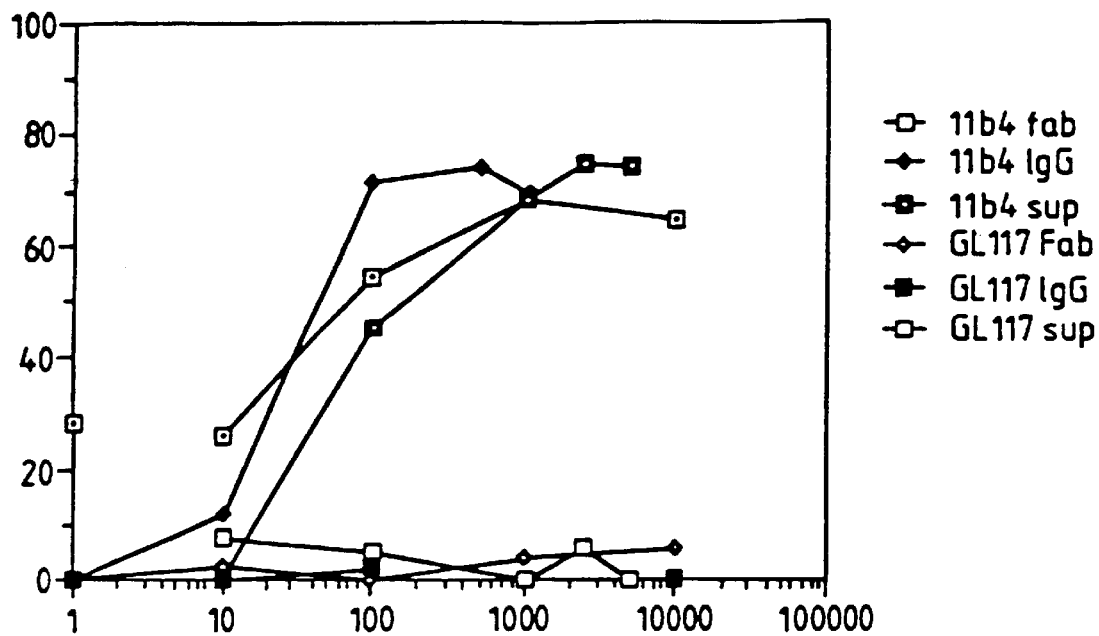
FIG. 3 (parts A and B) shows neutralization of $^{125}$I-CHO HuIL-4 binding to Daudi cells.

Table 1 below and FIG. 3A show the ability of 11B4 F(ab), IgG, and crude supernatant (unpurified antibody) to inhibit binding of $^{125}$I-HuIL-4 to Daudi cells. All three preparations inhibited binding to a maximum extent of 70%. The control monoclonal antibodies GL117 F(ab), IgG, and crude supernatant did not affect binding. (The control antibodies are to an unrelated antigen of the same idiotype.) The concentration of purified 11B4 IgG or F(ab) required to produce 50% inhibition of binding is in the range of 10–100 ng/ml.

Figure 3B:
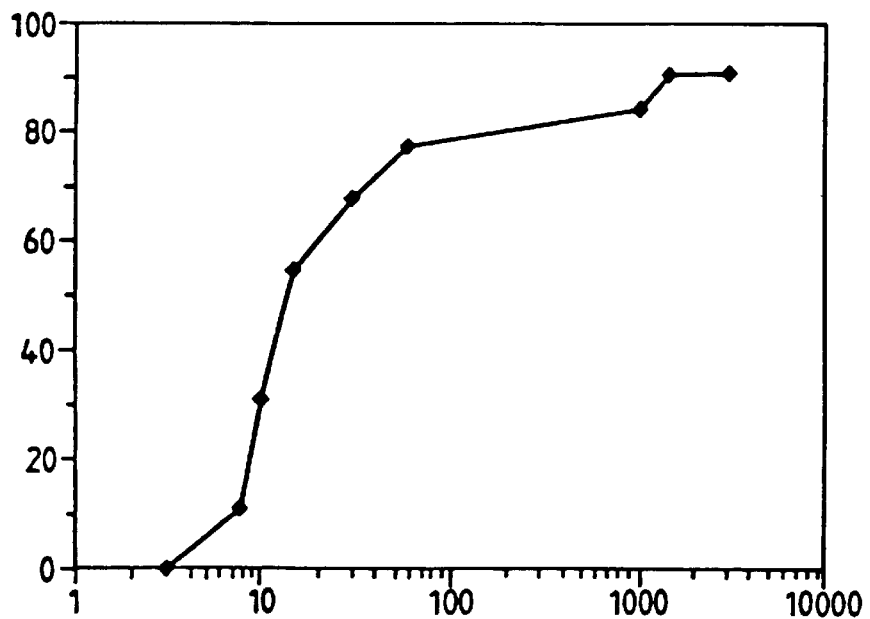

Table 2 below and FIG. 3B show the ability of 25D2.11 F(ab) to inhibit binding in the same assay. This preparation resulted in a 90% inhibition with a 50% maximum effect at 10–15 ng/ml.

In FIGS. 3A and 3B the X-axis shows ng/ml (in a log-scale) and the Y-axis shows percent inhibition.

In these experiments the HuIL-4 was prepared in Chinese hamster ovary cells and is designated CHO-HuIL-4 in the following Tables.

TABLE 1

Neutralization of $^{125}$I-CHO-HuIL-4 Binding To Daudi Cells by 11B4

| Sample | ng/ml | percent binding | Sample | ng/ml | percent binding |
|---|---|---|---|---|---|
| 11B4 F(ab) | 1 | 28 | 11B4 IgG | 1 | 0 |
|  | 10 | 25 |  | 10 | 12 |
|  | 100 | 54 |  | 100 | 71 |
|  | 1000 | 68 |  | 500 | 74 |
|  | 10000 | 65 |  | 1000 | 70 |
| 11B4 super-natant | 10 | 0 | GL117 F(ab) | 1 | 0 |
|  | 100 | 45 |  | 10 | 2.4 |
|  | 1000 | 68 |  | 100 | 0 |
|  | 2500 | 74 |  | 1000 | 3.7 |

TABLE 1-continued

Neutralization of $^{125}$I-CHO-HuIL-4 Binding To Daudi Cells by 11B4

| Sample | ng/ml | percent binding | Sample | ng/ml | percent binding |
|---|---|---|---|---|---|
| GL117 IgG | 5000 | 74 |  | 10000 | 5.8 |
|  | 1 | 0 | GL117 super-natant | 10 | 7.5 |
|  | 10 | 0 |  | 100 | 4.7 |
|  | 100 | 1.8 |  | 1000 | 0 |
|  | 1000 | 0 |  | 2500 | 5.5 |
|  | 10000 | 0 |  | 5000 | 0 |

TABLE 2

NEUTRALIZATION OF $^{125}$I-CHO-HuIL-4 BINDING TO DAUDI CELLS BY 25D2.11 F(ab) FRAGMENT

| ng/ml | percent inhibition | ng/ml | percent inhibition |
|---|---|---|---|
| 3000 | 90 | 15 | 54 |
| 1500 | 90 | 10 | 31 |
| 1000 | 84 | 7.5 | 10 |
| 60 | 77 | 3.0 | 0 |
| 30 | 67 |  |  |

Example VIII

Cloning of Antibody 25D2

General Methods and Reagents

Unless otherwise noted, standard recombinant DNA methods were carried out essentially as described by Maniatis et al., Molecular Cloning: A Laboratory Manual, 1982, Cold Spring Harbor Laboratory.

Small scale isolation of plasmid DNA from saturated overnight cultures was carried out according to the procedure of Birnboim et al. [Nuc. Acids Res. 7:1513 (1979)]. This procedure allows the isolation of a small quantity of DNA from a bacterial culture for analytical purposes. Unless otherwise indicated, larger quantities of plasmid DNA were prepared as described by Clewell et al. [J. Bacteriol. 110:1135 (1972)].

Specific restriction enzyme fragments derived by the cleavage of plasmid DNA were isolated by preparative electrophoresis in agarose. Gels measuring 9×5 ½ cm were run at 50 mA for 1 hour in Tris-Borate buffer (Maniatis et al., supra, p. 454) and then stained with 0.5 μg/ml ethidium bromide to visualize the DNA. Appropriate gel sections were excised, and the DNA was electroeluted (Maniatis et al., supra, p. 164). After electroelution, the DNA was phenol extracted (Maniatis et al., supra, p. 458) and ethanol precipitated (Maniatis et al., supra, p. 461).

Restriction enzymes and T4 DNA ligase were purchased from New England Biolabs (Beverly, Mass.). Superscript RNAse H$^-$ reverse transcriptase was from BRL/Gibco (Rockville, Md.), Taq DNA polymerase from Stratagene (LaJolla, Calif.), DNA polymerase Klenow fragment from Pharmacia LKB Biotechnology, Inc. (Piscataway, N.J.), calf intestinal phosphatase from Boehringer Mannheim Biochemicals (Indianapolis, Ind.) and RNAsin from Promega (Madison, Wis.). All enzymes were used in accordance with the manufacturers' instructions. The Sequenase version 2.0 sequencing system was obtained from United States Biochemical (Cleveland, Ohio).

Deoxynucleotide triphosphates and oligo $dT_{12-18}$ primer were from Pharmacia LKB Biotechnology, bovine serum albumin from Boehringer Mannheim Biochemicals and re-distilled phenol from BRL/Gibco.

The plasmid vector Bluescript was purchased from Stratagene, while competent *E. coli* strain DH5-alpha (Max Efficiency) was from BRL/Gibco.

Tissue culture media and supplements were from BRL/Gibco, and fetal calf serum was from Hyclone Laboratories, Inc. (Logan, Utah).

Cell Culture

Hybridoma cell line MP4.25D2.11 was maintained in RPMI 1640 medium supplemented with 10% heat-inactivated fetal calf serum, 2 mM glutamine and 10 units/ml penicillin/streptomycin in a humidified 37° C. chamber with 5% $CO_2$.

Isolation and Sequencing of Monoclonal Antibody 25D2

Medium conditioned by hybridoma cell line MP4.25D2.11 was concentrated 10–40 fold by ultrafiltration and then applied to a GAMMABIND G®-Agarose column in 0.01M sodium phosphate, pH 7.0, 0.15M NaCl, with 0.005% sodium azide. GammaBind G-Agarose is a beaded agarose to which recombinant streptococcal Protein G has been covalently immobilized. The bound protein was then eluted with 0.5M acetic acid adjusted to pH 3.0 with ammonium hydroxide. Fractions containing purified monoclonal antibody 25D2 were identified by sodium dodecylsulfate polyacrylamide gel electrophoresis (SDS-PAGE), essentially as described by Laemmli [Nature 227:680 (1970)].

Two methods were used to separate the heavy and light chains of purified antibody 25D2 for sequence determination. The first method employed semi-preparative SDS-PAGE followed by electroblotting onto a polyvinyldifluoride (PVDF) membrane. Briefly, 120 μg (800 pmoles) of the highly purified antibody were subjected to slab gel electrophoresis in SDS after reduction with 2-mercapto-ethanol (Laemmli, supra). The resolved heavy and light chains were then transferred onto an IMMOBILON® membrane (a PVDF membrane from Millipore, Bedford, Mass.), essentially using the electroblotting method of Matsudaira [J. Biol. Chem. 261:10035 (1987)]. The bands corresponding to the heavy and light chains were excised from the membrane following staining with Coomassie Brilliant Blue and processed for N-terminal sequencing.

The other method permitted larger amounts of the heavy and light chains to be isolated in solution. Using this method, a 6 ml sample of purified antibody 25D2 containing 1 mg/ml protein was dialyzed against 0.1M Tris-HCl, 1 mM EDTA, pH 8.0, at 4° C. and then subjected to oxidative sulfitolysis in $NaSO_3/Na_2S_2O_6$, essentially as described by Morehead et al. [Biochemistry 23:2500 (1984)]. Following sulfitolysis, the antibody preparation was dialyzed against 1M acetic acid, lyophilized to dryness, reconstituted in 1M acetic acid to a volume of 1.5 ml, and subjected to gel filtration in a 1×30 cm SEPHADEX G-75® column (Pharmacia, Piscataway, N.J.) equilibrated with the same buffer.

Fractions enriched in heavy and light chains were pooled separately and separately subjected to gel filtration in a 1.5×100 cm SEPHADEX G-75® column in 1M acetic acid. The purity of the heavy and light chains following this step was assessed by analytical SDS-PAGE. Fractions containing the heavy (4 nmoles) and light (3 nmoles) chains were pooled separately and concentrated in vacuo to about 0.1 ml-volumes for sequencing.

All N-terminal amino acid sequencing was performed using an Applied Biosystems Model 477A protein-peptide sequencer. Sequencing of the isolated heavy and light chains blotted onto the IMMOBILON® membrane was carried out essentially as described by Yuen et al. [Biotechniques 7:74 (1989)]. Analysis of the isolated chains in solution was performed following the instructions of the manufacturer of the sequencer. ps Oligonucleotide Primer Design and Cloning Strategy Based upon information obtained from the foregoing amino acid sequence analyses, degenerate oligonucleotide primers were designed for use in the polymerase chain reaction (PCR) method [Saiki et al., Science 239:487 (1988)]. One degenerate primer designated B1798 had a nucleotide sequence encoding the amino-terminal 13 amino acid residues of the mature heavy chain of 25D2. Another degenerate primer designated B1873 had a nucleotide sequence encoding the amino-terminal 7 amino acid residues of the mature light chain of the antibody.

A non-degenerate oligonucleotide primer designated B1797 having a nucleotide sequence corresponding to a segment in the 3' untranslated region of DNA encoding the antibody heavy chain [Bruggemann et al., Proc. Natl. Acad. Sci. USA 83:6075 (1986)] was also designed, as was a non-degenerate oligonucleotide primer designated B1868 having a nucleotide sequence corresponding to a segment in the kappa constant region of DNA encoding the antibody light chain [Sheppard et al., Proc. Natl. Acad. Sci. USA 78:7064 (1981)].

Other non-degenerate primers were designed for use in isolation of cDNA encoding the variable regions of the heavy and light chains of antibody 25D2, based upon nucleotide sequence information obtained following PCR amplification of cDNA encoding the complete heavy and light chains.

Oligonucleotide Synthesis

Oligonucleotide primers having sequences defined in the Sequence Listing were synthesized by standard methods using an Applied Biosystems Model 380B Synthesizer.

The designations of these primers, followed in parentheses by the corresponding sequence identification numbers, are as follows:

B1797 (SEQ ID NO: 5)
B1798 (SEQ ID NO: 6)
B1868 (SEQ ID NO: 7)
B1873 (SEQ ID NO: 8)
B1884 (SEQ ID NO: 9)
B1902 (SEQ ID NO: 10)
B1921 (SEQ ID NO: 11)
B1922 (SEQ ID NO: 12)
B1932 (SEQ ID NO: 13)
T3 (SEQ ID NO: 14)
T7 (SEQ ID NO: 15)

Primers B1798 and B1873 were designed to define a 5' NotI restriction site to facilitate cloning. Primers B1797 and B1868 were designed to define a 3' SpeI restriction site, for the same reason.

RNA Isolation

Total cytoplasmic RNA was isolated from hybridoma cell line MP4.25D2.11 by incubating the cells for 15 minutes in a lysis buffer consisting of 10 mM Tris-HCl, pH 7.4, 10 mM NaCl, 2 mM $MgCl_2$ and 0.5% Nonidet P40 (an octylphenol-ethylene oxide condensate containing an average of 9 moles ethylene oxide per mole of phenol). After a centrifugation step at 2,000×g for 5 minutes at 4° C., the nuclear pellet was discarded and the supernatant fluid was re-centrifuged at 10,000×g for 15 minutes at 4° C.

After the second centrifugation step, the supernatant fluid was mixed with an equal volume of a solution containing 200 mM NaCl, 10 mM Tris-HCl, pH 7.4, 20 mM ethylenediaminetetraacetate (EDTA) and 2% sodium dodecylsulfate (SDS). The mixture was extracted once with an equal volume of Tris-buffered phenol/chloroform (1:1) and once with chloroform. Following the extractions, the mixture was precipitated overnight with 1/20 volume of 0.2M sodium acetate, pH 5.5, and 2.5 volumes of absolute ethanol at −20° C.

First Strand Synthesis

First strand cDNA was synthesized directly from total cytoplasmic RNA at 37° C. for 90 minutes in a 10 µl reaction volume. The reaction mixture contained 5.6 µl of RNA in diethylpyrocarbonate-treated distilled $H_2O$, 0.25 µl of RNAsin (40,000 units/ml), 2 µl of 5X reverse transcriptase reaction buffer (250 mM Tris-HCl, pH 8.3, 200 mM KCl, 30 mM $MgCl_2$, 3 mM dithiothreitol), 0.25 µl of bovine serum albumin (4 mg/ml), 1 µl of 10 mM dNTP mixture (dATP, TTP, dCTP, dGTP), 0.4 µl of oligo dT primer (0.5 mg/ml) and 0.5 µl of Superscript RNase H⁻ reverse transcriptase (200 units/ml).

Polymerase Chain Reaction

PCR amplifications were carried out using a Techne programable thermal cycler. The PCR reaction mixtures consisted of 10 µl of first strand cDNA reaction mixture, 53.5 ml of distilled $H_2O$, 10 µl of 10X Taq polymerase reaction buffer (500 mM KCL, 100 mM Tris-HCl, pH 8.3, 15 mM $MgCl_2$, 0.1% gelatin), 16 µl of 1.25 mM dNTP mixture (dATP, TTP, dCTP, dGTP), 5 µl of each primer of interest (20 pmol/µl) and 0.5 µl of *Thermus aquaticus* DNA polymerase.

The PCR conditions included 30 cycles of: denaturation at 95° C. for 2 minutes, primer annealing at 37° C. for 2 minutes, primer extension at 72° C. for 3 minutes and a final extension period of 9 minutes at 72° C. At the end of amplification, 1 µl of 100 mM dNTP mixture and 1 µl of DNA polymerase Klenow fragment (5 units/µl) were added to each of the PCR reactions, and the fill-in step was allowed to proceed for 10 minutes at room temperature.

The PCR mixtures were subjected to electrophoresis in 1% agarose/Tris-borate gels containing 0.5 µg/ml ethidium bromide. The PCR fragments of interest were excised from the gels and purified by electroelution.

Subcloning and DNA Sequencing

The gel-purified PCR fragments were digested with NotI and SpeI and then ligated to dephosphorylated NotI/SpeI-digested Bluescript plasmid vector at 15° C. for 16–24 hours in a mixture containing 50 mM Tris-HCl, pH 7.5, 10 mM $MgCl_2$, 10 mM dithiothreitol, 50 µg/ml bovine serum albumin, 1 mM ATP and 10 units of T4 DNA ligase. Competent *E. coli* strain DH5-alpha (Max Efficiency) cells were transformed with the ligation mixture.

Diagnostic analysis of the resulting transformants was carried out by restriction digests with NotI and SpeI, as well as by PCR with the oligonucleotide primers used in the initial PCR reactions. The inserts of the subclones of interest were subjected to DNA sequencing using the Sequenase system.

Oligonucleotide primers T7, B1884, B1921 and B1922 were used to obtain DNA encoding the variable region of the heavy chain. Primers T3, B1902 and B1932 were used to obtain DNA encoding the variable region of the light chain.

CDR Determinations

The CDRs within the variable regions of the heavy and light chains of monoclonal antibody 25D2 were determined both by the method of Kabat et al., supra, and by computer binding site loop analysis. For the latter analysis, a Silicon Graphics Personal Iris Model 4D/25 computer was employed using Sybyl or IMPACT software. The approach taken involved essentially a combination of the three-dimensional modeling methods of Seville et al. [Biochemistry 27:8344 (1988)], the immunoglobulin hypervariable region conformation analytical methods of Chothia et al. [J. Mol. Biol. 196:901 (1987); Nature 342:877 (1989)] and the protein loop conformation analytical methods of Tramontano et al. [PROTEINS: Structure, Function and Genetics 6:382 (1989)].

Example IX

Antibody Humanization

General Methods and Reagents

Restriction enzymes and DNA modifying enzymes were from New England Biolabs. Taq polymerase was obtained from Perkin-Elmer Cetus, Inc. Mouse anti-human IgG4-Fc antibody was purchased from CalBiochem. Sheep anti-human IgG (H+L) peroxidase conjugate and human IgG4 protein standards were obtained from The Binding Site, Inc. Goat anti-rat IgG was purchased from Jackson Immuno-Research Labs.

Purified human IL4 (hIL4) was obtained from a bacterial expression system essentially as described by Lundell et al. [J. Indust. Microbiol. 5:215 (1990)] and radioiodinated by the IODOGEN® (Pierce Chemical Co.) method, according to the manufacturers instructions. A purified rat monoclonal antibody, designated 25D2, has been described by DeKruyff et al. [J. Exp. Med. 170:1477 (1989)].

Human growth hormone (hGH) standards and a goat anti-rabbit IgG peroxidase conjugate were purchased from Boehringer-Mannheim Biochemicals, Inc. Rabbit anti-hGH was from Dako Corp., and sheep anti-hGH was obtained from Biodesign International. Protein-G SEPHAROSE® CL-4B was purchased from Pharmacia, Inc. Oligonucleotides were synthesized using an Applied Biosystems (ABI) 380B DNA synthesizer.

Bacterial Strains, Plasmids, Cell Lines and Recombinant DNA Methods

All plasmids were propagated in *E. coli* K-12 strain MM294 (ATCC 33625). Bluescript (KS) and Bluescribe plasmids were obtained from Stratagene Inc. Plasmids pDSRS (ATCC 68232) and pSRS (ATCC 68234) are available from the American Type Culture Collection (ATCC). Plasmid HuCK encoding the human kappa constant region and plasmid p24BRH encoding the human IgG4 constant region were obtained from the ATCC (under Accession Nos. ATCC 59173 and ATCC 57413, respectively). Plasmid vectors pUC19 and pSV.Sport were from BRL/GIBCO (Gaithersburg, Md).

COS 7 cells obtained from the ATCC (ATCC CRL 1651) were propagated in Dulbecco's Modified Eagle's Medium (DMEM)/high glucose supplemented with 10% FBS and 6 mM glutamine. CHO cell line DXB11 was obtained from Dr. L. Chasin (Columbia University, NY, N.Y.) and was propagated before transfection in Ham's F12 medium supplemented with 10% FBS, 16 mM glutamine, 0.1 mM nonessential amino acids, 0.1 mM hypoxanthine and 0.016 mM thymidine. Transfected CHO cells were propagated in DMEM/high glucose supplemented with 10% dialyzed FBS, 18 mM glutamine, and 0.1 mM nonessential amino acids for selection.

A Jijoye cell line stably transformed by a recombinant vector comprising a human growth hormone reporter gene operably linked to a human germline ε transcript promoter (called C12 cells) and a Jijoye cell line expressing large quantities of the human IL-4 receptor on the cell surface (called CJ cells) were obtained from Dr. Chung-Her Jenh at Schering-Plough Corporation. Both cell lines were propagated in RPMI (Gibco) containing 15% horse serum, 5% FBS, 6 mM glutamine, 0.1 mM nonessential amino acids, 0.5 mg/ml geneticin (Gibco). Unless otherwise stated, recombinant DNA methods were performed as described by Maniatis et al., supra.

PCR was performed under standard conditions [Saiki et al., Science 230:1350 (1985)], and the sequences of fragments generated by PCR were confirmed by either manual or automated DNA sequencing. Manual DNA sequencing was performed with SEQUENASE® (United States Biochemical Co.) according to the manufacturer's instructions. Automated DNA sequencing was performed on an ABI 373A DNA sequencer using the Taq polymerase cycle sequencing kit provided by ABI, according to the manufacturer's recommendations. Plasmid DNA was prepared for transfections using Qiagen columns (Qiagen, Inc.), according to the manufacturer's instructions.

Determination of Antibody Concentrations by Enzyme-linked Immunosorbent Assay (ELISA)

Antibody concentrations were determined by an IgG4-specific ELISA. Briefly, Nunc MAXISORB® Immunoplates were coated at 4° C. for at least 4 hours with a mouse anti-human IgG4-Fc monoclonal antibody at 5 µg/ml in 50 mM bicarbonate buffer, pH 9.5. The plates were blocked for 1 hour at room temperature in Blocking buffer [3% bovine serum albumin (BSA) in Dulbecco's modified phosphate buffered saline (PBS; Gibco-BRL)]. After washing the plates with Wash buffer (10 mM potassium phosphate, pH 7.4, 0.05% Tween-20), serially diluted samples, either as purified antibodies or conditioned medium, in a volume of 100 µl were applied to the wells of the plates.

Conditioned medium containing the humanized antibodies was typically concentrated 10–30-fold by centrifugation filtration (Amicon, Inc) prior to assay. The plates were incubated for 1–2 hours at room temperature, after which the samples were aspirated and the wells were washed 3 times. Fifty microliters of anti-human IgG (H+L) peroxidase conjugate were added to each well and the plates were incubated for 1 hour at room temperature. The plates were then washed 3 times and 50 µl of ABTS peroxidase substrate (Boehringer-Mannheim Biochemicals) was added to each well for detection of the immune complexes. The plates were read spectrophotometrically at 405 nm.

Transfections

For each of the recombinant antibodies described below, 5 µg of both the heavy and light chain plasmids were transfected into 5×10⁶ COS 7 cells in a total volume of 250 µl by electroporation using a Biorad Gene Pulser. After 4 hours, the medium (DMEM plus 10% FBS) was replaced with DMEM minus serum. The cells were propagated for 72 hours, after which the medium was harvested, clarified by centrifugation, and stored at −20° C. for subsequent antibody purification. To obtain larger quantities of the humanized antibodies, recombinant CHO cell lines were established that produced antibodies designated h25D2-1 or h25D2-4.

To isolate stable CHO cell lines, 20 µg of the appropriate heavy and light chain plasmid DNAs [molar ratio of heavy chain plasmid:light chain plasmid (with the dhfr gene) 10:1] were transfected into 5×10⁶ CHO DXB11 cells by the calcium phosphate precipitation method [Graham et al., Virology 52:456 (1973)]. After two days, the cells were selected for resistance to hypoxanthine and thymidine starvation, i.e. dhfr expression [Schimke et al., Methods in Enzymology 151:85 (1987)].

Clones secreting antibody were identified by ELISA, expanded and subjected to methotrexate-mediated gene amplification. Clones secreting the greatest amount of antibody were expanded into roller bottles, and the serum-free medium was harvested continuously. Confluent roller bottle cultures were propagated in serum-containing medium for 48 hours, after which the cells were rinsed with Dulbecco's Modified PBS and the medium was replaced with a serum-free preparation. The serum-free medium was harvested after 3–4 days for subsequent antibody purification.

Antibody Purification

Serum-free conditioned medium containing the antibodies was passed over a Mab TRAP® column of streptococcal protein G-SEPHAROSE® CL-4B (Pharmacia), and the antibodies were eluted according to the manufacturer's instructions. Final antibody concentrations were determined by ELISA as described above.

Affinity Measurements

A. Affinity Constants

To determine whether the humanized antibodies were capable of binding human IL-4, apparent dissociation constants were determined by coating immunoplates with mouse anti-human IgG4-Fc (capture antibody) and blocking the plates as described above for the ELISA assay. After washing the wells, the plates were incubated at room temperature for 2 hours with concentrated conditioned medium containing one of the humanized antibodies (100 µl/well). Wild-type rat antibody 25D2 was assayed in parallel for comparison, using an anti-rat IgG as the capture antibody.

The wells were washed and incubated with $^{125}$I-hIL-4 at concentrations between 4,000 and 2 pM in final volumes of 100 µl. All assays were performed in triplicate, and the background binding was determined by using a 1000-fold molar excess of unlabelled hIL4 in control wells.

After incubation for 2 hours at room temperature, the wells were washed, the protein was solubilized in 75 µl of Solubilization buffer [0.1N NaOH/1% sodium dodecylsulfate (SDS)], and the solution was counted in an LKB gamma counter.

Concentrations of bound and free hIL4 were determined, and the affinities of the antibodies were determined by Scatchard plot analysis [Berzofsky et al., in *Fundamental Immunology*, 1984, Paul, E. E., Ed., Raven Press, New York, N.Y., pp. 595–644].

B. Competitive Binding Analysis

A comparison of antigen binding by wild-type rat antibody 25D2 and the humanized antibodies was made using a plate binding competition assay in which the binding of labelled human IL-4 ($^{125}$I-hIL-4) to plates coated with antibody 25D2 was measured in the presence of unlabelled antibody 25D2, humanized antibody h25D2-1 or humanized antibody h25D2-4, all of which had been purified.

Immunosorb plates were coated with a 60 ng/ml solution of the rat 25D2 antibody diluted in PBS (100 µl/well) for at least 16 hours at 4° C. The wells were then blocked with Blocking buffer (3% BSA in PBS) for 4 hours at room temperature. Fifty microliters of 2-fold serially diluted competing antibodies plus the appropriate amount of $^{125}$I-hIL-4 (50 µl total volume) were added to each well, and the plates were incubated at room temperature for 16–24 hours. The plates were washed 3 times with potassium phosphate, pH 7.4, plus 0.05% Tween 20. The wells were aspirated dry, and 75 µl of Solubilization buffer (0.1N NaOH/1% SDS) was added to each well and incubated for 30 minutes at room temperature. The solution was removed from each well and counted in an LKB gamma counter.

Inhibition of Receptor Binding

The humanized antibodies were assayed for the ability to inhibit the binding of radiolabelled hIL-4 to the recombinant human IL-4 receptor expressed on Jijoye CJ cells in microtiter plates. Briefly, the humanized antibodies were serially diluted in cell growth medium at protein concentrations of from 8.6 nM to 4 pM. Rat antibody 25D2 was similarly diluted and used as a positive control. Jijoye CJ cells ($10^5$ cells) and 44 pM $^{125}$I-hIL-4 were then added to each well (200 μl final volume per well) and the plates were incubated for 2 hours at 4° C.

After the incubation, the contents of the wells were mixed and 185 μl were removed and layered onto sucrose cushions (150 μl of 5% sucrose in growth medium plus 0.02% sodium azide). After centrifugation (1500 rpm, 4° C., 10 minutes), the tubes were quick-frozen in liquid nitrogen, and the bottoms of the tubes containing the cell pellets were clipped and counted in a gamma counter. Bound cpm was plotted vs. the antibody concentration, and the humanized antibodies were compared to the native antibody at the concentrations required to cause 50% inhibition of receptor binding ($IC_{50}$).

Germline Epsilon Promoter Reporter Gene Assay

Jijoye C12 cells were seeded into 96 well dishes at a density of $4 \times 10^5$ cells/125 μl/well in medium. Serially diluted test antibodies and 1 ng/mL hIL-4 were added to the cells, and the plates were incubated at 37° C. for about 64 hours. After the incubation, 100 μl of the conditioned medium were removed from each well and added to individual wells of an immunoplate previously coated with a 1:2000 dilution of sheep anti-human growth hormone (αhGH) in sodium carbonate buffer, pH 9.5. The plates were incubated at room temperature for 2 hours and washed 5 times with 10 mM potassium phosphate buffer containing 0.05% Tween-20. One hundred microliters of a rabbit ahGH (diluted 1:1000) were added to each well, and incubation was continued for 1 hour.

The wells were washed again as described above, and 100 μl of a horse-radish peroxidase conjugated goat anti-rabbit IgG (diluted 1:10,000) was added to each well. After washing, 50 μl of ABTS peroxidase substrate was added to the wells for detection of the immune complexes. The plates were read spectrophotometrically at 405 nm.

Optical density (O.D.) at 405 nm was plotted vs. antibody concentration, and the humanized antibodies were compared to the native antibody at the concentrations required to cause 50% inhibition of the expression of the human growth hormone under the control of the germline ε promoter ($IC_{50}$).

Humanized Antibodies

Homology Modeling

Using the methods described above, it was determined that antibody LAY was an optimal human framework candidate. LAY heavy and light chain pairs were first pursued.

A listing of potential minimal and maximal 25D2 residues that could be grafted into the framework sequences were determined by the above-described methods to be as shown in Table 3.

TABLE 3

| | Residues[a] |
|---|---|
| $V_H$ Minimal List: | 28, 30, 31, 32, 53, 54, 56, 100, 101, 103, 105, 106, 107 |
| $V_H$ Maximal List[b]: | 33, 35, 50, 51, 52, 57, 58 59, 61, 65, 109, 110 |

TABLE 3-continued

| | Residues[a] |
|---|---|
| $V_L$ Minimal List: | 29, 30, 31, 50, 52, 91, 94 |
| $V_L$ Maximal List[b]: | 24, 34, 46, 49, 53, 54, 56 |

[a]Residues for $V_H$ and $V_L$ refer to the residue numbers in SEQ ID NO: 1 and SEQ ID NO: 2, respectively.
[b]The $V_H$ and $V_L$ Maximal Lists include the corresponding Minimal Lists and the further indicated residues.

Specific constructs described below contain the following residues from the foregoing Table:

TABLE 4

| Humanized Antibody | Residues | |
|---|---|---|
| h25D2H-1, L | $V_H$ LAY Maximal; | $V_L$ LAY Maximal |
| h25D2H-1, L-1 | $V_H$ LAY Maximal; | $V_L$ LAY Maximal (less residues 46 and 49) |
| h25D2H-2, L-1 | $V_H$ LAY Maximal; (less residues 33 and 35) | $V_L$ LAY Maximal (less residues 46 and 49) |
| h25D2H-3, L-1 | $V_H$ LAY Maximal; (less residues 28 and 30) | $V_L$ LAY Maximal (less residues 46 and 49) |
| h25D2H-4, L-1 | $V_H$ LAY Maximal; (less Residues 28, 30 and 65) | $V_L$ LAY Maximal (less residues 46 and 49) |
| h25D2H-5, L-1 | $V_H$ LAY Maximal; (less residues 33, 35 and 65) | $V_L$ LAY Maximal (less residues 46 and 49) |

Construction of Humanized 25D2 Light Chain Expression Vectors

The nucleotide sequence of DNA for an initial version of the humanized 25D2 light chain (h25D2L), including (from 5' to 3') fifteen 5' noncoding bases and bases encoding an initiating methionine residue, a leader sequence and the variable region of the antibody, together with the corresponding amino acid sequence of the leader and the antibody, is defined in the Sequence Listing by SEQ ID NO: 16.

In the construction of this humanized light chain, silent restriction endonuclease cleavage sites were deduced from the Genetics Computer Group (GCG; Madison, Wis.) SILENT MAP® program. Nucleotide sequences selected to encode the protein sequence utilized codons found in the rat 25D2 sequence, although several codons were changed to create restriction endonuclease cleavage sites.

The entire variable region of the antibody was cloned as three contiguous DNA fragments that were synthesized as pairs of oligonucleotides. These pairs of oligonucleotides were amplified by PCR and joined at unique restriction endonuclease cleavage sites. The result was three fragments (numbered from 5' to 3') delineated by EcoRI/KpnI (fragment 1), KpnI/PstI (fragment 2) and PstI/MscI (fragment 3) sites. In the amplification reactions, the two oligonucleotides in each pair were complementary to each other over a stretch of 18–24 nucleotides. Therefore each oligonucleotide served as a template for the other.

The designations of these oligonucleotide primers, followed in parentheses by the corresponding sequence identification numbers, were as follows:

2481 (SEQ ID NO: 17)
2482 (SEQ ID NO: 18)
2700 (SEQ ID NO: 19)
2641 (SEQ ID NO: 20)
2483 (SEQ ID NO: 21)

2491 (SEQ ID NO: 22)
2662 (SEQ ID NO: 23)
2661 (SEQ ID NO: 24)

The synthesis of fragment 1 required two PCR amplifications. An initial PCR using primers 2481 and 2482 generated a fragment lacking a translational initiation sequence and the leader peptide coding sequence. This fragment was reamplified with primers 2700 and 2641 to add on an EcoRI site followed by the translational initiation and leader peptide coding sequences. The final fragment 1 thus contained at it's 5' terminus an EcoRI site followed by a translational initiation sequence [Kozak, Nucleic Acids Res. 12:857 (1984)] and a sequence encoding a leader peptide corresponding to the anti-CAMPATH-1 antibodies [Reichmann et al., Nature 332:323 (1988)].

The fragment 1 sequence extended through a KpnI site and encoded amino acid residues 1–36 of the variable region of the humanized light chain. Fragment 2 encoded residues 36–79 of the humanized light chain, including a KpnI and PstI site at the 5' and 3' termini, respectively. Fragments 1 and 2 were joined at the unique KpnI site and subcloned into the Bluescript (KS) vector between the EcoRI and PstI sites in the vector to create fragment 1–2. Fragment 3 encoded the remaining amino acids of the variable domain (residues 78–106) and extended from the PstI site through an MscI site (located 22 bases upstream of the 3' terminus of the variable domain), and included an EcoRI site at the 3' end.

Fragment 3 was subcloned into a Bluescript (KS) vector between the PstI and EcoRI sites in the vector. A 321 bp fragment (fragment 4) containing 22 nucleotides at the 3' end of the humanized variable region, including the MscI site, joined to the coding sequence for the entire human kappa constant region, was generated by PCR using the HuCK plasmid as template and primers 2856 and 2857, the sequences of which are defined by SEQ ID NO: 25 and SEQ ID NO: 26, respectively. In addition to the MscI site at the 5' end of fragment 4, an EcoRI site was included on the 3' end to facilitate cloning.

Fragment 4 was joined to fragment 3 between the common MscI site within the variable region and the EcoRI site present on the 3' end of fragment 4 and the vector. An EcoRV site was present downstream of fragment 3–4 in the vector. Fragment 3–4 was removed as a PstI/EcoRV fragment and was ligated to fragment 1–2 between the common PstI site in the variable region and the blunt-ended SmaI site in the vector. The entire coding region for the h25D2L light chain could be obtained after cleavage at the SalI and BamHI sites flanking the coding region in the Bluescript vector.

The mammalian expression vector was constructed by first cleaving the Bluescript vector containing the h25D2L sequence at the 3' end with BamHI, and then treating the cleavage product with Klenow fragment DNA polymerase, under conditions that left flush ends. Next, the h25D2L DNA fragment was obtained after cleavage at the 5' end with SalI. Finally, the h25D2L coding region was ligated to vector pDSRS which had previously been digested with SalI and SmaI. The completed vector, designated pSDh25L, contained the entire coding region for the humanized 25D2 antibody including the signal peptide and the human kappa constant region.

Co-transfection of the foregoing h25D2L DNA with a heavy chain DNA (designated h25D2H-1; prepared as described below) into COS 7 cells did not produce measurable antibody expression, although antibody expression was observed when the h25D2L DNA was co-transfected with DNA for a humanized heavy chain from an unrelated antibody (data not shown).

Since the h25D2L light chain was capable of being expressed with an unrelated heavy chain, it was possible that the sequence of either the humanized 25D2 light chain or the humanized heavy chain was inhibiting h25D2 antibody expression.

Examination of the Fv interface of the 25D2 molecular model suggested that replacement of the human LAY residues leucine 46 and tyrosine 49 with animal residues phenylalanine 46 and phenylalanine 49 could affect the ability of h25D2L to combine with the heavy chain. In addition, comparison of human kappa chain variable region sequences in the Swiss-Prot protein database (Bairoch, Amos) revealed that the leucine at amino acid position 46 and the tyrosine at amino acid position 49 were highly conserved. Therefore, the foregoing humanized light chain gene was reconstructed to introduce mutations at these positions. In addition, an arginine residue at position 107 that had been omitted in the h25D2L DNA was replaced.

To modify the h25D2L DNA, two pairs of oligonucleotide primers were synthesized to perform PCR-based mutagenesis of the h25D2L coding region. Primer 3016 (SEQ ID NO: 28), which was used as the 5' primer, encompassed the coding region for amino acid residues 38–51 of the light chain variable domain and included a StuI site at the 5' end. Primer 3016 also incorporated three nucleotide changes into the h25D2L sequence. This resulted in replacement of a phenylalanine residue with a leucine residue (F46L) at position 46 of the amino acid sequence, and replacement of a phenylalanine residue at position 49 with a tyrosine codon (F49Y) at position 49. A 3' primer designated 3017 (SEQ ID NO: 29) encompassed the PstI site at position 237.

A 126 bp fragment was generated by PCR using oligonucleotide primers 3016 and 3017 and the h25D2L Bluescript plasmid as template DNA. The StuI/PstI PCR fragment was used to replace the corresponding fragment in vector h25D2L, thereby incorporating the F46L, F49Y changes.

An oligonucleotide primer designated 3018 (used as a 5' primer; SEQ ID NO: 30) was synthesized which encompassed amino acid residues 95–106 of the light chain variable region, including the MscI site at the 5' terminus, and the first three residues of the human kappa constant region. In addition, a codon for arginine (R107) was inserted at the junction of the variable and constant regions in the primer. Another primer designated 3019 (SEQ ID NO: 31) was synthesized to serve as a 3' primer. This primer corresponded to sequences in the Bluescript vector including the BamHI and SpeI sites.

Figure 4:
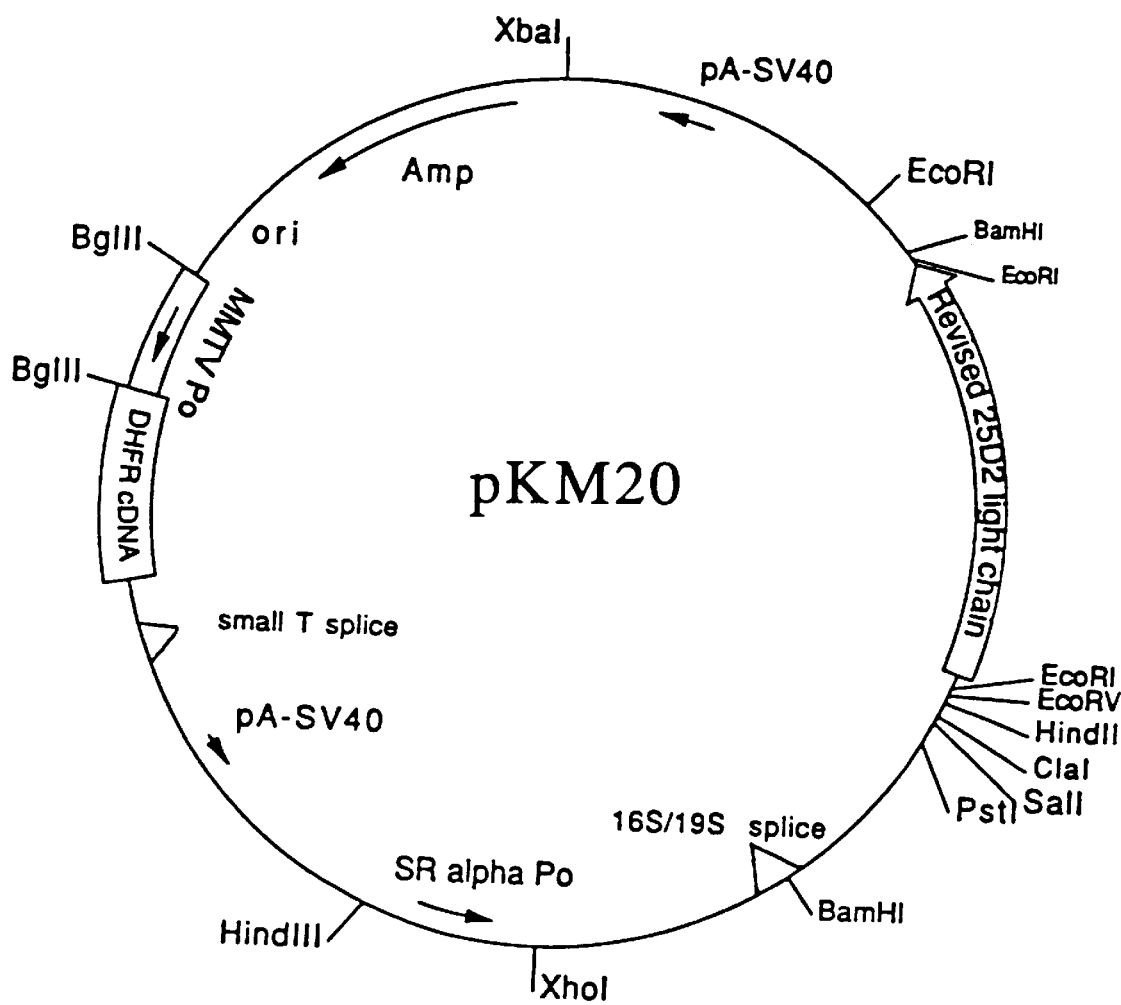
FIG. 4 is a schematic representation of plasmid pKM20.

Using primers 3018 and 3019 and the h25D2L Bluescript plasmid as template, a fragment was generated by PCR that included residues 95–107 of the variable domain and the entire coding region of the human kappa chain. This MscI/SpeI PCR fragment was used to replace the corresponding fragment in the F46L, F49Y vector described above. After confirming the DNA sequence of the PCR fragments, the vector was digested with SpeI and treated with Klenow fragment DNA polymerase under conditions that generated flush-ended termini. A fragment containing the entire coding region of humanized antibody light chain h25D2L-1 was isolated after SalI digestion and ligated to the pDSRS vector previously digested with SalI and SmaI. The resulting h25D2L-1 expression vector containing the F46L, F49Y, and R107 mutations of h25D2L is shown schematically in FIG. 4.

The nucleotide sequence of the DNA for the modified version of the humanized 25D2 light chain, including (from 5' to 3') fifteen 5' noncoding bases and bases encoding an initiating methionine residue, a leader sequence and the variable region of the antibody, together with the corresponding amino acid sequence of the leader and the antibody, is defined in the Sequence Listing by SEQ ID NO: 27.

Construction of Humanized 25D2 Heavy Chain Expression Vectors

The nucleotide sequence of DNA for an initial version of the humanized 25D2 heavy chain (h25D2H-1), including (from 5' to 3') fifteen 5' noncoding bases and bases encoding an initiating methionone residue, a leader sequence and the variable region of the antibody, together with the corresponding amino acid sequence of the leader and the antibody, is defined in the Sequence Listing by SEQ ID NO: 32. The nucleotide sequences that were selected to encode the protein sequence, including the signal peptide, utilized codons found in the rat 25D2 sequence. Several codons were changed to create restriction endonuclease cleavage sites.

The entire variable region was cloned as three contiguous DNA fragments that were synthesized as pairs of oligonucleotides. These pairs of oligonucleotides were amplified by the PCR and joined at unique restriction endonuclease cleavage sites. The result was three fragments (numbered from 5' to 3') delineated by SalI/SmaI (fragment 1), SmaI/PstI (fragment 2) and PstI/ApaI (fragment 3) sites. In the amplification reactions, the two oligonucleotides in each pair were complementary to each other over a stretch of 18–24 nucleotides. Therefore each oligonucleotide served as a template for the other.

The designations of these oligonucleotide primers and the corresponding SEQ ID NOs defining their sequences were as follows:

| Oligonucleotide | SEQ ID NO. |
|---|---|
| 2588 | 33 |
| 2589 | 34 |
| 2232 | 35 |
| 2445 | 36 |
| 2446 | 37 |
| 2447 | 38 |
| 2523 | 39 |
| 2580 | 40 |
| 2642 | 41 |
| 2646 | 42 |

The synthesis of fragment 1 required two amplification reactions. An initial PCR product of primers 2588 and 2599 was subjected to a second round of amplification with oligonucleotides 2232 and 2445, to yield fragment 1. The final fragment 1 thus contained at its 5' terminus a SalI site followed by a translational initiation sequence (Kozak, supra) and a sequence encoding the leader peptide corresponding to the anti-CAMPATH-1 antibodies (Reichmann et al., supra). The fragment 1 sequence extended through a SmaI site and included the coding sequence for amino acid residues 1–42 of the variable region of the humanized heavy chain.

Fragment 2 encoded residues 42–82 of the humanized heavy chain, including a SmaI site and a PstI site at the 5' and 3' ends, respectively. Fragments 1 and 2 were joined at the unique SmaI site and subcloned into the Bluescript (KS) vector between the SalI and PstI sites in the vector, to create plasmid pBS1-2.

Fragment 3 encoded the remaining amino acids of the variable domain (residues 81–121) and extended from the PstI site through the 3' terminus of the variable region and on through thirty nucleotides of the coding sequence for the human IgG4 constant region. A unique ApaI site was located within sixteen nucleotides of the IgG4 constant sequence in fragment 3. The synthesis of fragment 3 also required two amplification reactions. An initial PCR product of primers 2523 and 2580 was subjected to a second round of amplification with primers 2642 and 2646, to yield fragment 3.

To prepare an initial heavy chain expression vector, plasmid p24BRH was cleaved with ApaI and SacI, and an ApaI/SacI fragment containing IgG4 genomic DNA was isolated. Fragment 3 was ligated to a common ApaI site on the isolated fragment from plasmid p24BRH. A resulting PstI/SacI fragment (encompassing residues 81–121 of the h25D2H-1 variable region joined to IgG4 DNA encoding the complete IgG4 constant region) was then ligated to a Bluescribe plasmid that had previously been cleaved with PstI and SacI, to produce a plasmid designated pAS6.

The IgG4 genomic DNA was then replaced with the cDNA. First, a plasmid containing the IgG4 cDNA inserted between the PstI and NotI sites of the pSV.Sport vector was cleaved at the PstI site in the vector upstream of the cDNA and at a BstEII site within the IgG4 cDNA. This plasmid had been constructed as follows.

Oligonucleotide primers corresponding to the entire heavy chain variable region (V$_H$) of an unrelated humanized antibody were synthesized by standard methods. The designations of these oligonucleotides and the corresponding SEQ ID NOs defining their sequences were as follows:

| Oligonucleotide | SEQ ID NO. |
|---|---|
| B2474CC | 43 |
| B2419CC | 44 |
| B2420CC | 45 |
| B2475CC | 46 |
| B2477CC | 47 |
| B2479CC | 48 |

Pairs of oligonucleotides B2474CC and B2419CC, B2420CC and B2475CC, B2477CC and B2479CC were heat-denatured, annealed, and incubated with Taq polymerase or Pfu (Stratagene, La Jolla, Calif.). In the polymerase chain reactions (PCRs), the two oligonucleotides in each pair were complementary to each other by about 24 to 30 nucleotides.

Therefore, each oligonucleotide served as the template for the other.

The PCRs were carried out for 18 cycles, after which the three resulting DNA fragments, corresponding to the three consecutive segments of V$_H$, designated V$_H$1, V$_H$2 and V$_H$3, were electrophoresed in an agarose gel and purified by electroelution.

The relative order of the three V$_H$ DNA fragments, restriction sites for cloning, and the multicloning-site map of cloning vector used, pSV.Sport, were as follows:

| Fragment | Restriction Sites | PCR Primers |
|---|---|---|
| V$_H$1 | EcoRI____SpeI | B2474CC + B2419CC |
| V$_H$2 | SpeI____XbaI | B2420CC + B2475CC |
| V$_H$3 | EcoRI/XbaI____SalI/ApaI/SstI | B2477CC + B2479CC |

Multi-cloning Sites of pSV.Sport

PstI/KpnI/RsrII/EcoRI/SmaI/SalI/SstI/SpeI/NotI/XbaI/BamHI/HindIII/SnaBI/MluI

Fragment V$_H$1 was restricted with enzymes EcoRI and SpeI and cloned into vector pSV.Sport. Fragment V$_H$2 was subsequently joined to V$_H$1 in pSV.Sport by directional insertion at SpeI and XbaI sites. Fragment VH3 was separately cloned into pSV.Sport as an EcoRI/XbaI-SalI/ApaI/SstI fragment. The three fragments were verified by DNA sequencing.

Full-length VH cDNA of the unrelated antibody was assembled by first joining VH3 to a genomic DNA of the γ4 H-chain constant region (CH) and then attaching the VH3-CH fragment to the VH1-VH2 fragment, as is described more fully below.

To facilitate synthesis and secretion of the heavy chain, a coding sequence for a leader peptide was inserted into the DNA. The amino acid and nucleotide sequences of this leader are those of the leader of the anti-CAMPATH-1 antibodies (Reichmann et al., supra).

To construct DNA encoding a full-length antibody H-chain, the VH synthetic cDNA was combined with human γ4 constant-region genomic DNA (ATCC 57413) using ApaI restriction cleavage and ligation. This procedure was initiated by digesting plasmid pSV.Sport containing VH3 with NotI followed by treatment with Klenow DNA polymerase (Boehringer Mannheim) to generate blunt ends. The resulting DNA was ethanol-precipitated, resuspended, and digested with ApaI. This restricted plasmid DNA was ligated with the ApaI/SmaI restriction fragment of the genomic γ4 constant region.

The VH3-CH genomic DNA was then excised as an XbaI/HindIII fragment and inserted into pSV.Sport already containing VH1-VH2, thereby completing assembling of the full-length heavy chain DNA.

In subsequent manipulations, a human γ4 constant-region cDNA was designed and constructed to replace the genomic DNA. This was accomplished using six oligonucleotide PCR primers that were synthesized by standard methods. The designations of these oligonucleotides and the corresponding SEQ ID NOs defining their sequences were as follows:

| Oligonucleotide | SEQ ID NO. |
|---|---|
| B2491CC | 49 |
| B2498CC | 50 |
| B2499CC | 51 |
| B2597CC | 52 |
| B2598CC | 53 |
| B2656CC | 54 |

Primers B2491 CC, B2499CC and B2598CC corresponded to the plus strand of γ4 constant region cDNA. Primers B2498CC, B2597CC and B2656CC corresponded to the minus strand. Using human γ4 genomic DNA as the template, three consecutive double-stranded DNA fragments encompassing the entire γ4 constant-region coding cDNA were generated by PCR.

The three CH DNA segments, restriction sites for cloning, and primers used were as follows:

| Segment | Restriction Sites | PCR Primers |
|---|---|---|
| CH A. | SalI_____EcoRI | B2491CC + B2498CC |
| CH B. | EcoRI_____XhoI/SalI | B2499CC + B2500CC |
| CH C. | SalI/XhoI_____NotI | B2598CC + B2656CC |

Segment A was cloned into pUC19 as a SalI/EcoRI restriction fragment. Segment C, as a SalI/XhoI-NotI restriction fragment, was cloned into pSV.Sport. Segment B, as an EcoR1-Xho1/Sal1 fragment, was cloned into pSV.Sport already containing segment C. All three segments were verified by DNA sequencing.

The γ4 cDNA was assembled by excising segment A with PstI and EcoRI, and cloning this fragment into pSV.Sport already containing segments B and C. The restriction map of the human γ4 CH cDNA and its relative position in pSV.Sport multi-cloning sites are as follows:

A        B       C
PstI/SalI ••• EcoRI ••• XhoI ••• NotI/HindIII/SnaBI/MluI

The γ4 CH cDNA was excised as a SalI-HindIII fragment to replace the genomic γ4 fragment in the previously described full-length H-chain construct. The final product was the pSVSPORT-1 vector that was cleaved as described above.

Next, plasmid pAS6 was linearized with PstI and partially digested with BstEII within the IgG4 sequence. A fragment containing a segment of the coding sequences of the variable region from the PstI site (amino acid residues 81–121) and the IgG4 cDNA to the BstEII site (residues 122–191) was isolated and subcloned into the pSV.Sport containing the IgG4 cDNA, between the PstI and BstEII sites. The construct, designated pAS7, encompassed residues 81–121 of the variable region joined to the entire IgG4 cDNA flanked by a 5' PstI site and a 3' XbaI site.

Figure 5:
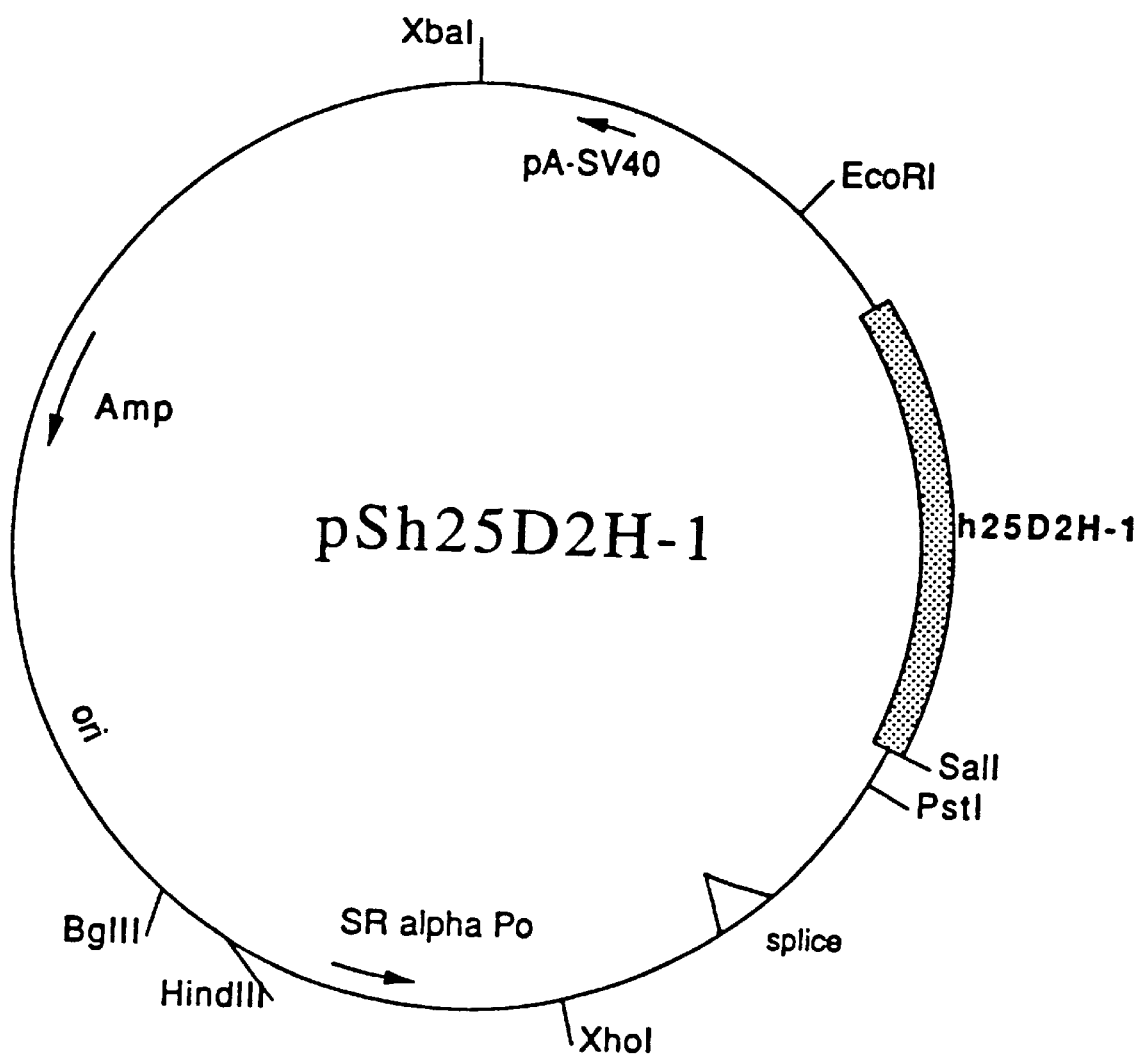
FIG. 5 is a schematic representation of plasmid pSh25D2H-1.

Plasmid pAS7 was cleaved with PstI and XbaI, and the fragment (containing residues 81–121 of the variable region and the IgG4 constant region cDNA) was subcloned into vector pBS1–2 (containing fragment 1–2) between the PstI and XbaI sites. This vector, designated pDA5, was then linearized with SacI and treated with T4 DNA polymerase under conditions that left flush ends. The entire coding region of the h25D2H-1 heavy chain was isolated after SalI digestion and ligated to vector pSRS, which had previously been cleaved with SalI and SmaI. The final plasmid, designated pSh25D2H-1, is shown schematically in FIG. 5.

Four variants of the h25D2H-1 heavy chain (designated h25D2H-through were constructed. The amino acid changes incorporated into the four variants are indicated in FIG. 6, in which amino acid residues are shown using standard single-letter abbreviations, and the sequences within CDRs 1, 2 and 3 of antibody 25D2 and the variants are aligned with those of antibody LAY. Residues not shown were those of the corresponding position in antibody LAY.

The sequence identification numbers of the amino acid sequences within CDRs 1, 2 and 3 of antibody LAY, antibody 25D2, humanized heavy chain h25D2H-1 and variants thereof (see FIG. 6) are as follows:

CDR1
  LAY (SEQ ID NO: 61)
  25D2 (SEQ ID NO: 64)
  h25D2H-1 (SEQ ID NO: 64)
  h25D2H-2 (SEQ ID NO: 67)
  h25D2H-3 (SEQ ID NO: 68)
  h25D2H-4 (SEQ ID NO: 68)
  h25D2H-5 (SEQ ID NO: 67)
CDR2
  LAY (SEQ ID NO: 62)
  25D2 (SEQ ID NO: 65)
  h25D2H-1 (SEQ ID NO: 65)
  h25D2H-2 (SEQ ID NO: 65)
  h25D2H-3 (SEQ ID NO: 65)
  h25D2H-4 (SEQ ID NO: 69)
  h25D2H-5 (SEQ ID NO: 69)

CDR3
  LAY (SEQ ID NO: 63)
  25D2 (SEQ ID NO: 66)
  h25D2H-1 (SEQ ID NO: 66)
  h25D2H-2 (SEQ ID NO: 66)
  h25D2H-3 (SEQ ID NO: 66)
  h25D2H-4 (SEQ ID NO: 66)
  h25D2H-5 (SEQ ID NO: 66)

All of the additional heavy chain variants were constructed by replacing DNA restriction endonuclease fragments from plasmid pDA5 with double-stranded oligonucleotide cassettes containing the desired mutations. In each cassette, the nucleotide sequences chosen to encode the protein sequence maintained the codons that were used in the original version, except that some codons were altered to incorporate the amino acid changes and also to introduce a unique restriction endonuclease cleavage site for selection of positive transformants.

To construct h25D2H-2, an oligonucleotide cassette comprising oligonucleotides designated 3112 (SEQ ID NO: 55) and 3116 (SEQ ID NO: 56) containing a "silent" NheI site was used to replace the BamHI/SmaI DNA fragment in pDA5, and the new plasmid was designated pKM21. To create h25D2H-3, the DNA of pKM21 was cleaved with NheI and SmaI, releasing CDR 1. This NheI/SmaI CDR 1 DNA fragment was then replaced with an oligonucleotide cassette comprising oligonucleotides 3117 (SEQ ID NO: 57) and 3118 (SEQ ID NO: 58), to generate pKM23 containing the h25D2H-3 sequence.

Vectors pKM21 and pKM23 were cleaved with SalI and SmaI, and the fragments containing the altered CDR 1 sequences were isolated and subsequently used to replace the corresponding CDR 1 DNA fragment in vector pSh25H-1. The resulting expression vectors encoding the h25D2H-2 and h25D2H-3 heavy chains were designated pSh25H-2 and pSh25H-3, respectively.

To construct the h25D2H-4 coding sequence, plasmid pKM23 was cleaved with MscI and PstI to release a DNA fragment encompassing CDR 2. Plasmid pKM21 was similarly prepared with MscI and PstI to construct the h25D2H-5 coding sequence. An oligonucleotide cassette comprising oligonucleotides 3119 (SEQ ID NO: 59) and 3120 (SEQ ID NO: 60) encompassing the altered CDR 2 was inserted between the MscI and PstI sites in both plasmids, to generate h25D2H-4 and h25D2H-5, respectively.

The resulting plasmids were digested with SacI and treated with T4 DNA polymerase under conditions that left flush ends. The coding regions for the h25D2H-4 and h25D2H-5 heavy chains were isolated following SalI cleavage and subcloned into vector pSRS which had previously been digested with SalI and SmaI. The final vectors were designated pSh25H-4 and pSh25H-5, respectively.

Expression and Purification of the Humanized Antibodies

All of the humanized antibody DNAs were transfected into COS 7 cells by electroporation, and the medium was replaced with serum-free medium four hours after transfection. The cells were propagated in serum-free medium for 3 days, after which the medium was harvested. To obtain greater amounts of the humanized antibodies, stable CHO cell lines were established that produced the h25D2-1 and the h25D2-4 antibodies.

The appropriate heavy chain plasmid (pSh25H-1 and pSh25H-4. respectively) was co-transfected with the pKM20 light chain plasmid at a ratio of 10:1 into CHO DXB11 cells. Of approximately 40 clones selected for resistance to hypoxanthine and thymidine starvation, greater than 50% tested positive for h25D2-1 antibody expression in a human IgG4 ELISA assay.

Twelve of the clones producing the greatest amount of antibody h25D2-1 were subjected to methotrexate-mediated DNA amplification. Six of these clones (designated h25D2-1 #1, #7, #15, #17, #18 and #21) were selected for growth in the presence of 100–250 nM methotrexate. The levels of antibodies expressed by these clones was estimated based on ELISA to be about 200–700 ng/$10^6$ cells/day. Clone #17 clone was expanded into roller bottle culture to obtain greater quantities of the h25D2-1 antibody for purification and characterization.

Approximately 40 clones transfected with the h25D2-4 plasmids were also selected for resistance to hypoxanthine and thymidine starvation. About 30% of these clones tested positive for antibody expression in a human IgG4 ELISA assay. The positive clones were grown in the presence of 5 nM methotrexate. The antibody level of one of the h25D2-4 clones (designated clone #7A) was estimated by IgG4 ELISA to be about 50–100 ng/$10^6$ cells/day. This clone was expanded into roller bottle culture to produce greater quantities of antibody h25D2-4 for purification and characterization.

Serum-free conditioned medium containing antibodies produced by CHO cell clones in roller bottle culture was harvested continuously as described above. Antibodies in the conditioned medium were partially purified by protein G-SEPHAROSE® chromatography. Analysis of the antibodies by reducing SDS-PAGE showed a high degree of purity (at least about 90%). Analysis of the antibodies by a series of ELISA assays that showed that they contained both human k and γ4 constant regions.

Example X

Antibody Characterization

Affinity Constants

All five variants of the humanized heavy chain gene were independently co-transfected into COS 7 cells with the pKM20 light chain vector. The serum-free conditioned medium was harvested after 72 hours and concentrated. Affinity constants were determined as described above, with the results shown in Table 5.

TABLE 5

| Antibody | Source* | Coating Antibody | Apparent $K_d$ |
| --- | --- | --- | --- |
| h25D2-1 | COS CM | α hIgG4 Fc | 4 nM |
| h25D2-2 | COS CM | α hIgG4 Fc | 29 nM |
| h25D2-3 | COS CM | α hIgG4 Fc | 5 nM |
| h25D2-4 | COS CM | α hIgG4 Fc | 5 nM |
| h25D2-5 | COS CM | α hIgG4 Fc | 31 nM |
| 25D2 | Purified | α rat IgG Fc | 1 nM |

*COS CM = COS cell conditioned medium.

As shown in Table 5, the affinities of humanized antibodies h25D2-1, h25D2-3 and h25D2-4 for binding to human IL-4 were similar to that of the native rat 25D2 antibody. The affinities of antibodies h25D2-2 and h25D2-5 antibodies were lower.

Competitive Binding Analysis

To further characterize humanized antibody variants h25D2-1 and h25D2-4, competitive binding assays with the humanized antibodies and rat antibody 25D2 were performed as described above. The results showed that at room temperature antibody h25D2-1 was 3-fold less effective than antibody 25D2 in competing with antibody 25D2 for binding to $^{125}$I-hIL-4. Antibody h25D2-4 was about 100-fold less effective than antibody 25D2 in the same assay. When the same assays were carried out at 4° C., however, humanized antibody h25D2-1 was as effective in the competition assay as the native antibody, and antibody h25D2-4 was only 2-fold less effective.

Receptor Binding Inhibition

Humanized antibodies h25D2-1 and h25D2-4 antibodies were assayed as described above for the ability to inhibit binding of radiolabeled hIL-4 to recombinant hIL-4 receptors expressed on the Jijoye CJ cell line. With a constant concentration of the radiolabeled hIL-4, the concentration of antibodies h25D2-1 and h25D2-4 required to cause 50% inhibition of receptor binding ($IC_{50}$) was calculated to be 0.5–1.0 and 1.0–2.0 nM, respectively. The $IC_{50}$ for the native 25D2 antibody was determined to be 0.5–1.0 nM.

Inhibition of Germline Epsilon Promoter Activity

Jijoye C12 cells contain multiple endogenous copies of a human growth hormone reporter gene operably linked to a germline $\epsilon$ transcript promoter. This promoter is inducible by IL-4 [Rothman et al., J. Exp. Med. 168:2385 (1988)].

To determine whether antibodies h25D2-1 and h25D2-4 could block induction by human IL-4 of the germline $\epsilon$ promoter, assays were carried out using Jijoye C12 cells as described above. $IC_{50}$ values for antibodies h25D2-1 and h25D2-4 were found to be about 120 and 600 pM, respectively, compared to a range of 20–40 pM observed for wild-type antibody 25D2.

Hybridoma Deposits

Hybridomas IC1.11B4.6 and MP4.25D2.11 were deposited Sep. 29, 1987 and Sep. 1, 1988, respectively, with the American Type Culture Collection, Rockville, Md., USA (ATCC), under accession numbers ATCC HB 9550 and ATCC HB 9809, respectively. These deposits were made under conditions as provided under ATCC's agreement for Culture Deposit for Patent Purposes, which assures that the deposits will be made available to the US Commissioner of Patents and Trademarks pursuant to 35 USC 122 and 37 CFR 1.14 and will be made available to the public upon issue of a U.S. patent, and which requires that the deposits be maintained. Availability of the deposited strains is not to be construed as a license to practise the invention in contravention of the rights granted under the authority of any government in accordance with its patent laws.

Many modifications and variations of this invention can be made without departing from its spirit and scope, as will become apparent to those skilled in the art. The specific embodiments described herein are offered by way of example only, and the invention is to be limited only by the terms of the appended claims.

What is claimed is:

1. A polypeptide comprising a variable region having the amino acid sequence of the variable region selected from the group consisting of h25D2H-1, h25D2H-2, h25D2H-3, h25D2H-4 and h25D2H-5.

2. A polypeptide comprising a variable region having the amino acid sequence of the variable region h25D2L-1.

3. A protein that specifically binds to human interleukin 4 which:

a) is selected from the group consisting of a binding composition, a single-chain binding protein, and a humanized monoclonal antibody; and b) comprises an antibody chain variable region having the amino acid sequence of the variable region selected from the group consisting of h25D2L-1, h25D2H-1, h25D2H-2, h25D2H-3, h25D2H-4 and h25D2H-5.

4. A humanized monoclonal antibody which comprises a variable region of an antibody, having the amino acid sequence selected from the group consisting of h25D2L-1, h25D2H-1, h25D2H-2, h25D2H-3, h25D2H-4 and h25D2H-5.

5. A pharmaceutical composition comprising a protein of claim 3 and a physiologically acceptable carrier.

* * * * *